US008119348B2

(12) United States Patent
Swaroop et al.

(10) Patent No.: US 8,119,348 B2
(45) Date of Patent: Feb. 21, 2012

(54) COMPOSITIONS AND METHODS FOR DIAGNOSING AND TREATING MACULAR DEGENERATION

(75) Inventors: Anand Swaroop, Gaithersburg, MD (US); Goncalo Abecasis, Ann Arbor, MI (US); Wei Chen, Ann Arbor, MI (US); Dwight Stambolian, Sewell, NJ (US); Albert O. Edwards, Eugene, OR (US)

(73) Assignees: The Regents of the University of Michigan, Ann Arbor, MI (US); The Trustees of the University of Pennsylvania, Philadelphia, PA (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 12/834,529

(22) Filed: Jul. 12, 2010

(65) Prior Publication Data
US 2011/0014716 A1 Jan. 20, 2011

Related U.S. Application Data

(60) Provisional application No. 61/224,753, filed on Jul. 10, 2009.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ....... 435/6.1; 435/91.2; 536/23.1; 536/24.3

(58) Field of Classification Search .................. None
See application file for complete search history.

(56) References Cited

U.S. PATENT DOCUMENTS

| | | |
|---|---|---|
| 5,538,848 A | 7/1996 | Livak et al. |
| 5,639,606 A | 6/1997 | Willey et al. |
| 5,643,765 A | 7/1997 | Willey et al. |
| 5,876,978 A | 3/1999 | Willey et al. |
| 5,962,223 A | 10/1999 | Whiteley et al. |
| 6,417,342 B1 | 7/2002 | Stone et al. |
| 6,593,104 B1 | 7/2003 | Stone et al. |
| 7,011,952 B2 | 3/2006 | Hageman et al. |
| 7,108,982 B1 | 9/2006 | Hageman |
| 7,309,487 B2 | 12/2007 | Inana et al. |
| 7,312,050 B2 | 12/2007 | Hageman et al. |
| 7,344,846 B2 | 3/2008 | Hageman et al. |
| 7,351,524 B2 | 4/2008 | Hageman et al. |
| 7,351,534 B2 | 4/2008 | Klein et al. |
| 7,682,804 B2 | 3/2010 | Hageman et al. |
| 7,745,389 B2 | 6/2010 | Hageman et al. |
| 2002/0015957 A1 | 2/2002 | Hageman et al. |
| 2002/0102581 A1 | 8/2002 | Hageman et al. |
| 2006/0263819 A1 | 11/2006 | Hageman et al. |
| 2008/0146501 A1 | 6/2008 | Hageman et al. |
| 2008/0261211 A1 | 10/2008 | Allikmets et al. |
| 2008/0274453 A1 | 11/2008 | Hageman et al. |
| 2008/0280825 A1 | 11/2008 | Hageman et al. |
| 2008/0318264 A1 | 12/2008 | Hageman et al. |
| 2009/0124542 A1 | 5/2009 | Hageman et al. |

OTHER PUBLICATIONS

Hegele R.A. Arterioscler Thromb Vasc Biol. 2002;22:1058-1061.*
Juppner H. Bone (Aug. 1995) vol. 17 No. 2, Supplment pp. 39S-42S.*
Pennisi E. Science (Sep. 18, 1998) vol. 281, No. 5384, pp. 1787-1789.*
Abecasis et al., "Age-related macular degeneration: a high-resolution genome scan for susceptibility loci in a population enriched for late-stage disease," Am J Hum Genet, 74, pp. 482-494 (2004).
Anderson and Young, Quantitative Filter Hybridization, in Nucleic Acid Hybridization (1985).
Chamberlin et al., "New RNA polymerase from *Escherichia coli* infected with bacteriophage T7," Nature, 228, pp. 227-231 (1970).
Clark et al., "His-384 allotypic variant of factor H associated with age-related macular degeneration has different heparin binding properties from the non-disease-associated form," J Biol Chem, 281, pp. 24713-24720 (2006).
Congdon et al., "Causes and prevalence of visual impairment among adults in the United States," Arch Ophthalmol, 122, pp. 477-485 (2004).
Devlin et al., "Genomic control for association studies," Biometrics, 55, pp. 997-1004 (1999).
Dewan et al., "HTRA1 promoter polymorphism in wet age-related macular degeneration," Science, 314, pp. 989-992 (2006).
Edwards et al., "Complement factor H polymorphism and age-related macular degeneration," Science, 308, pp. 421-424 (2005).
Fagerness et al., "Variation near complement factor I is associated with risk of advanced AMD," Eur J Hum Genet, 17, pp. 100-104 (2009).
Feng et al., "Regulation of neurotransmitter release by synapsin III," J Neurosci, 22, pp. 4372-4380 (2002).
Fisher et al., "Meta-analysis of genome scans of age-related macular degeneration," Hum Mol Genet, 14, pp. 2257-2264 (2005).
Fritsche et al., "Age-related macular degeneration is associated with an unstable ARMS2 (LOC387715) mRNA," Nat Genet, 40, pp. 892-896 (2008).
Gold et al., "Variation in factor B (BF) and complement component 2 (C2) genes is associated with age-related macular degeneration," Nat Genet, 38, pp. 458-462 (2006).
Gunderson et al., "Whole-genome genotyping," Methods in Enzymology, 410, 359-376 (2006).
Hageman et al., "A common haplotype in the complement regulatory gene factor H (HF1/CFH) predisposes individuals to age-related macular degeneration," Proc Natl Acad Sci USA, 102, pp. 7227-7232 (2005).
Haines et al., "Bringing the genetics of macular degeneration into focus," PNAS, 104(43), pp. 16725-16726 (2007).
Haines et al., "Complement factor H variant increases the risk of age-related macular degeneration," Science, 308, pp. 419-421 (2005).

(Continued)

*Primary Examiner* — Stephen Kapushoc
(74) *Attorney, Agent, or Firm* — Casimir Jones, S.C.

(57) ABSTRACT

The present invention relates generally to biomarkers for macular degeneration. In particular, the present invention provides a plurality of biomarkers for monitoring and diagnosing macular degeneration. The compositions and methods of the present invention find use in diagnostic, therapeutic, research, and drug screening applications.

6 Claims, 18 Drawing Sheets

OTHER PUBLICATIONS

Hollyfield et al., "Oxidative damage-induced inflammation initiates age-related macular degeneration," Nat Med, 14, pp. 194-198 (2008).
Jackson et al., "Photoreceptor degeneration and dysfunction in aging and age-related maculopathy," Ageing Res Rev, 1, pp. 381-396 (2002).
Jager et al., "Age-related macular degeneration," N Engl J Med, 358, pp. 2606-2617 (2008).
Jakobsdottir et al., "Interpretation of genetic association studies: markers with replicated highly significant odds ratios may be poor classifiers," PLoS Genet, 5, e1000337 (2009).
Jakobsdottir et al., "Susceptibility genes for age-related maculopathy on chromosome 10q26," Am J Hum Genet, 77, pp. 389-407 (2005).
Kacian et al., "A replicating RNA molecule suitable for a detailed analysis of extracellular evolution and replication," Proc Natl Acad Sci USA, 69, pp. 3038-3042 (1972).
Kanda et al., "A variant of mitochondrial protein LOC387715/ARMS2, not HTRA1, is strongly associated with age-related macular degeneration," PNAS, 104, pp. 16227-16232 (2007).
Kathiresan et al., "Common variants at 30 loci contribute to polygenic dyslipidemia," Nat Genet, 41, pp. 56-65 (2009).
Klein et al., "Complement factor H polymorphism in age-related macular degeneration," Science, 308, pp. 385-389 (2005).
Klein et al., "The relationship of cardiovascular disease and its risk factors to age-related maculopathy. The Beaver Dam Eye Study," Ophthalmology, 100, pp. 406-414 (1993).
Li et al., "CFH haplotypes without the Y402H coding variant show strong association with susceptibility to age-related macular degeneration," Nat Genet, 38, pp. 1049-1054 (2006).
Li et al., "Genotype imputation," Annu Rev Genomics Hum Genet, 10, pp. 387-406 (2009).
Malek et al., "Apolipoprotein B in cholesterol-containing drusen and basal deposits of human eyes with age-related maculopathy," Am J Pathol, 162, pp. 413-425 (2003).
Maller et al., "Common variation in three genes, including a noncoding variant in CFH, strongly influences risk of age-related macular degeneration," Nat Genet, 38, pp. 1055-1059 (2006).
Maller et al., "Variation in complement factor 3 is associated with risk of age-related macular degeneration," Nat Genet, 39, pp. 1200-1201 (2007).
Moreira et al., "7-Ketocholesterol is present in lipid deposits in the primate retina: potential implication in the induction of VEGF and CNV formation," Invest Ophthalmol Vis Sci, 50, pp. 523-532 (2009).
Mullins et al., "Drusen associated with aging and age-related macular degeneration contain proteins common to extracellular deposits associated with atherosclerosis, elastosis, amyloidosis, and dense deposit disease," FASEB J, 14, pp. 835-846 (2000).
Neale et al., "Germline genomic variants associated with childhood acute lymphoblastic leukemia," Nature Genetics, 41, pp. 1001-1005 (2009).
Price et al., "Principal components analysis corrects for stratification in genome-wide association studies," Nat Genet, 38, pp. 904-909 (2006).
Rivera et al., "Hypothetical LOC387715 is a second major susceptibility gene for age-related macular degeneration, contributing independently of complement factor H to disease risk," Hum Mol Genet, 14, pp. 3227-3236 (2005).
Schmidt et al., "Cigarette smoking strongly modifies the association of LOC387715 and age-related macular degeneration," Am J Hum Genet, 78, pp. 852-864 (2006).
Seddon et al., "Prediction model for prevalence and incidence of advanced age-related macular degeneration based on genetic, demographic, and environmental variables," Invest Ophthalmol Vis Sci, 50, pp. 2044-2053 (2009).
Swaroop et al., "Genetic susceptibility to age-related macular degeneration: a paradigm for dissecting complex disease traits," Hum Mol Genet, 16 Spec No. 2, pp. R174-R182 (2007).
Swaroop et al., "Unraveling a multifactorial late-onset disease: from genetic susceptibility to disease mechanisms for age-related macular degeneration," Annu Rev Genomics Hum Genet, 10, pp. 19-43 (2009).
Thornton and McPeek, "Case-control association testing with related individuals: a more powerful quasi-likelihood score test," Am J Hum Genet, 81, pp. 321-327 (2007).
Tomany et al., "Risk factors for incident age-related macular degeneration: pooled findings from 3 continents," Ophthalmology, 111, pp. 1280-1287 (2004.
Tserentsoodol et al., "Intraretinal lipid transport is dependent on high density lipoprotein-like particles and class B scavenger receptors," Mol Vis, 12, pp. 1319-1333 (2006).
Weber et al., "Mutations in the tissue inhibitor of metalloproteinases-3 (TIMP3) in patients with Sorsby's fundus dystrophy," Nat Genet, 8, pp. 352-356 (1994).
Willer et al., "Newly identified loci that influence lipid concentrations and risk of coronary artery disease," Nat Genet, 40, pp. 161-169 (2008).
Wu et al., "The ligation amplification reaction (LAR)—amplification of specific DNA sequences using sequential rounds of template-dependent ligatio," Genomics, 4, pp. 560-569 (1989).
Yates et al., "Complement C3 variant and the risk of age-related macular degeneration," N Engl J Med, 357, pp. 553-561 (2007).
Zarepasi et al., "Strong association of the Y402H variant in complement factor H at 1q32 with susceptibility to age-related macular degeneration," Am J Hum Genet, 77, pp. 149-153 (2005).
Ng, T.K. et al., "Multiple Gene Polymorphisms in the Complement Factor H Gene Are Associated with Exudative Age-Related MacularDegeneration in Chinese" Investigative Ophthalmology and Visual Science. 2008 49 (8):3312-3317.
Spencer, K.L. et al., "Deletion of CFHR3 and CFHR1 genes in age-related macular degeneration" Human Molecular Genetics, 2007 17(7): 971-977.
Brantley, M.A. Jr. et al., "Clinical Phenotypes Associated with the Complement Factor H Y402H Variant in Age-related Macular Degeneration" American Journal of Ophthamology 2007, 144(3):404-408.
Raychaudhuri, S. et al., "Associations of CFHR1—CFHR3 deletion and a CFH SNP to age-related macular degeneration are not independent" Nature Genetics 2010, 42(7):553-555.
Goto, AT. et al., "Genetic analysis of typical wet-type age-related macular degeneration and polypoidal choroidal vasculopathy in Japanese population." Journal of Ocular Biology, Diseases, and Informatics, 2009 2(4): 164-175.
Erlich H.A. (ed.), PCR Technology: Principles and Applications for DNA Amplification, Stockton Press, (1989).

* cited by examiner

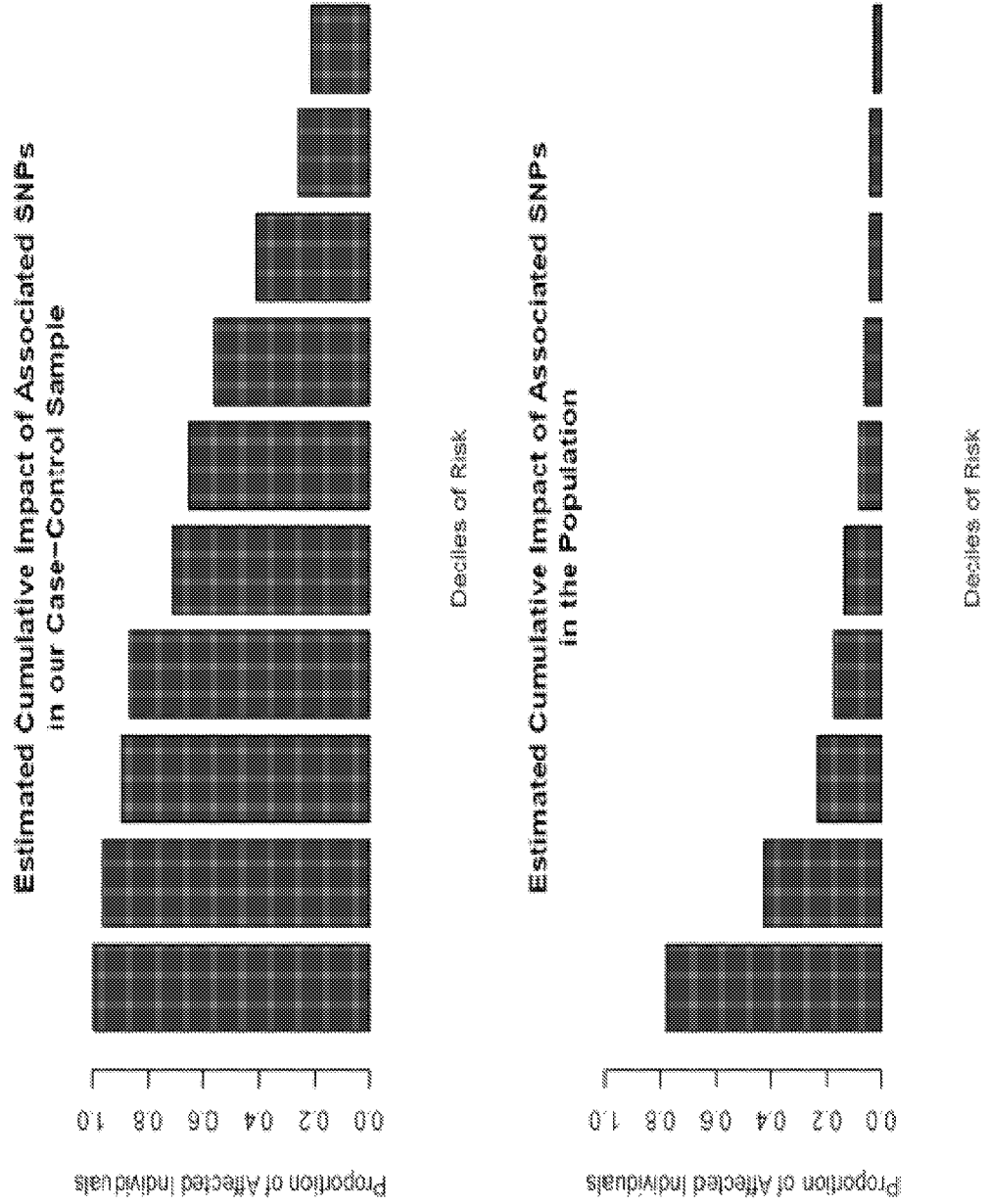

COMPOSITIONS AND METHODS FOR DIAGNOSING AND TREATING MACULAR DEGENERATION

CROSS-REFERENCE TO RELATED APPLICATION

The present application claims priority to U.S. Provisional Application 61/224,753, filed Jul. 10, 2009, which is herein incorporated by reference in its entirety.

GOVERNMENT SUPPORT

This invention was made with government support under grant numbers EY014467, EY016862, and EY012279 awarded by the National Institutes of Health. The government has certain rights in the invention.

FIELD OF THE INVENTION

The present invention relates generally to biomarkers for macular degeneration. In particular, the present invention provides a plurality of biomarkers for monitoring and diagnosing macular degeneration. The compositions and methods of the present invention find use in diagnostic, therapeutic, research, and drug screening applications.

BACKGROUND OF THE INVENTION

Age-related macular degeneration (AMD; OMIM 603075), a progressive neurodegenerative disease, is the most common cause of blindness in the elderly population of developed countries (Swaroop et al. Annu Rev Genomics Hum Genet 10, (in press) (2009), Congdon et al. Arch Opthalmol 122, 477-85 (2004), herein incorporated by reference in their entireties). The disease affects primarily the macular region of the retina, which is necessary for sharp central vision. An early hallmark of AMD is the appearance of drusen, which are extracellular deposits of proteins and lipids under the retinal pigment epithelium (RPE). As the disease progresses, the drusen grow in size and number. In advanced stages of AMD, atrophy of the RPE (geographic atrophy) and/or development of new blood vessels (neovascularization) result in central vision loss due to the death of photoreceptors (Swaroop et al. Annu Rev Genomics Hum Genet 10, (in press) (2009), Jager, et al. N Engl J Med 358, 2606-17 (2008), Jackson et al. Ageing Res Rev 1, 381-96 (2002), herein incorporated by reference in their entireties).

In recent years, progress has been made in identifying genetic contributors to AMD susceptibility. A series of genetic linkage scans provided strong evidence for multiple susceptibility loci, notably on chromosomes 1q31 and 10q26 (Fisher et al. Hum Mol Genet 14, 2257-64 (2005), herein incorporated by reference in its entirety). Disease associated variants near complement factor H (CFH, 1q32) and a gene of poorly understood function (ARMS2, 10q26) were soon identified at these two loci through a combination of genomewide association scans (Klein et al. Science 308, 385-9 (2005), Dewan et al. Science 314, 989-92 (2006), herein incorporated by reference in their entireties) and fine-mapping of linkage signals (Rivera et al. Hum Mol Genet 14, 3227-36 (2005), Jakobsdottir et al. Am J Hum Genet 77, 389-407 (2005), Haines, et al. Science 308, 419-21 (2005), Edwards et al. Science 308, 421-4 (2005), herein incorporated by reference in their entireties). Discovery of association between AMD and the CFH locus was particularly transforming, leading to the identification of additional susceptibility loci including C2/CFB, C3, and CFI (Fagerness et al. Eur J Hum Genet 17, 100-4 (2009), Gold et al. Nat Genet 38, 458-62 (2006), Maller et al. Nat Genet 39, 1200-1 (2007), Yates et al. N Engl J Med 357, 553-61 (2007).), herein incorporated by reference in their entireties).

SUMMARY

In some embodiments, the present invention provides a method for characterizing a subject's risk for developing age-related macular degeneration (AMD) comprising detecting the presence of or the absence of one or more polymorphisms on or near the genes CFH, ARMS2/HTRA1, C2/CFB, C3, CFI, SYN3/TIMP3, and LIPC. In some embodiments, the polymorphisms are one or more of rs10737680, rs3793917, rs429608, rs2230199, rs2285714, rs1329424, rs9380272, rs9621532, and rs493258, alone, or in combination with other markers (e.g. known markers), or alternatively detection of polymorphisms or sequences in linkage disequilibrium with any of the above markers. In some embodiments, the method comprises detecting the presence of or the absence of two or more polymorphisms. In some embodiments, the method comprises detecting the presence of or the absence of five or more polymorphisms. In some embodiments, the method comprises detecting the presence of or the absence of seven or more polymorphisms. In some embodiments, the method comprises detecting the presence of or the absence of nine polymorphisms. In some embodiments, detection of said one or more polymorphisms (e.g. 1, 2, 3, 4, 5, 6, 7, 8, 9, 10, >10) indicates an elevated risk of developing AMD.

In some embodiments, the present invention provides a panel of AMD markers. In some embodiments, the present invention comprises a panel of two or more AMD markers. In some embodiments, the present invention comprises a panel of three or more AMD markers. In some embodiments, the present invention comprises a panel of four or more AMD markers. In some embodiments, the present invention comprises a panel of five or more AMD markers. In some embodiments, the present invention comprises a panel of six or more AMD markers. In some embodiments, the present invention comprises a panel of seven or more AMD markers. In some embodiments, the present invention comprises a panel of eight or more AMD markers. In some embodiments, the present invention comprises a panel of nine or more AMD markers.

In some embodiments, the present invention comprises a panel of markers comprising the AMD marker rs10737680 and any combination of AMD markers disclosed herein or elsewhere. In some embodiments, the present invention comprises a panel of markers comprising the AMD marker rs3793917 and any combination of AMD markers disclosed herein or elsewhere. In some embodiments, the present invention comprises a panel of markers comprising the AMD marker rs429608 and any combination of AMD markers disclosed herein or elsewhere. In some embodiments, the present invention comprises a panel of markers comprising the AMD marker rs2230199 and any combination of AMD markers disclosed herein or elsewhere. In some embodiments, the present invention comprises a panel of markers comprising the AMD marker rs2285714 and any combination of AMD markers disclosed herein or elsewhere. In some embodiments, the present invention comprises a panel of markers comprising the AMD marker rs1329424 and any combination of AMD markers disclosed herein or elsewhere. In some embodiments, the present invention comprises a panel of markers comprising the AMD marker rs9380272 and any combination of AMD markers disclosed herein or elsewhere. In some embodiments, the present invention comprises a panel of markers comprising the AMD marker rs9621532 and any combination of AMD markers disclosed herein or elsewhere. In some embodiments, the present invention comprises a panel of markers comprising the AMD marker rs493258 and any combination of AMD markers disclosed herein or elsewhere.

In some embodiments, the present invention provides a kit comprising, consisting essentially of, or consisting of reagents and components useful, sufficient, or necessary for detection markers of AMD. In some embodiments, a kit comprises, consists essentially of, or consists of reagents and components for detection of 100 or fewer markers of AMD. In some embodiments, a kit comprises, consists essentially of, or consists of reagents and components for detection of 50 or fewer markers of AMD. In some embodiments, a kit comprises, consists essentially of, or consists of reagents and components for detection of 20 or fewer markers of AMD. In some embodiments, a kit comprises, consists essentially of, or consists of reagents and components for detection of 10 or fewer markers of AMD. In some embodiments, a kit comprises, consists essentially of, or consists of reagents and components for detection of 2 or more of rs10737680, rs3793917, rs429608, rs2230199, rs2285714, rs1329424, rs9380272, rs9621532, and rs493258. In some embodiments, a kit comprises, consists essentially of, or consists of reagents and components for detection of 4 or more of rs10737680, rs3793917, rs429608, rs2230199, rs2285714, rs1329424, rs9380272, rs9621532, and rs493258. In some embodiments, a kit comprises, consists essentially of, or consists of reagents and components for detection of 6 or more of rs10737680, rs3793917, rs429608, rs2230199, rs2285714, rs1329424, rs9380272, rs9621532, and rs493258. In some embodiments, a kit comprises, consists essentially of, or consists of reagents and components for detection of 8 or more of rs10737680, rs3793917, rs429608, rs2230199, rs2285714, rs1329424, rs9380272, rs9621532, and rs493258.

BRIEF DESCRIPTION OF THE DRAWINGS

The foregoing summary and detailed description is better understood when read in conjunction with the accompanying drawings which are included by way of example and not by way of limitation.

FIG. 5 shows multi-locus genotypes and disease risk; the top panel summarizes the proportion of affected individuals in each risk decile, with the highest risk decile on the left, when sample is segregated according to the risk of disease predicted by a simple logistic regression model. The bottom panel makes equivalent predictions at the population level, after weighting cases and controls to take into account that the sample is enriched for cases.

DEFINITIONS

Figure 1:
FIG. 1 shows a summary of genome-wide association scan results: The top panel summarizes the significance of the association signal at each examined SNP in the discovery samples; evidence for association was evaluated using a simple logistic regression model, with disease status as the outcome, and age, sex, two principal components of ancestry, and imputed minor allele count as predictors; the five loci that are confirmed are highlighted in green; the two new loci with $p<5\times10-8$ after follow-up are highlighted in blue; the bottom panel displays a quantile-quantile plot for test statistics and shows that, consistent with our genomic control value of 1.007, there is little evidence for inflation of test statistics due to unmodelled relatedness or population structure; the shaded region in the bottom panel corresponds to a 90% confidence interval for the test statistics, estimated using 1000 null replicates.
Figure 1:
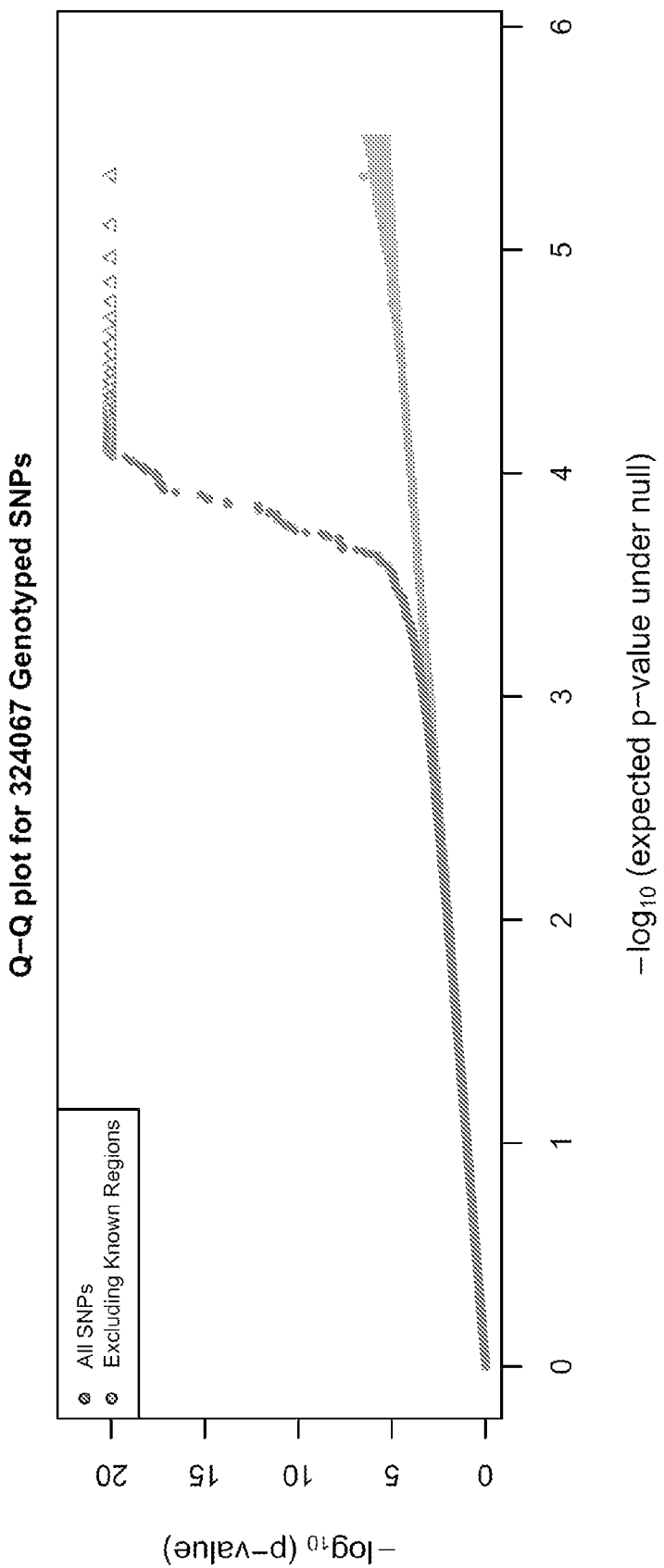

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having AMD" refers to a subject that presents one or more symptoms indicative of age-related macular degeneration, has one or more risk factors for AMD, or is being screened for AMD (e.g., during a routine physical). A subject suspected of having AMD has generally not been tested for AMD, or has not had a recent test which indicated the subject suffers from AMD. However, a "subject suspected of having AMD" encompasses an individual who has received a preliminary diagnosis but for whom a confirmatory test has not been done. A "subject suspected of having AMD" is sometimes diagnosed with AMD and is sometimes found to not have AMD.

As used herein, the term "subject diagnosed with AMD" refers to a subject who has been tested and found to have AMD. AMD may be diagnosed using any suitable method, including but not limited to, the diagnostic methods of the present invention.

As used herein, the term "subject suffering from AMD" refers to a subject who has AMD and exhibits one or more symptoms thereof. A subject suffering from AMD may or may not have received a diagnosis, and may or may not be aware of the condition.

As used herein, the term "initial diagnosis" refers to a test result of initial AMD diagnosis that reveals the presence or absence or risk of AMD. An initial diagnosis does not include information about the stage or extent of AMD.

As used herein, the term "subject at risk for AMD" refers to a subject with one or more risk factors for developing AMD. Risk factors include, but are not limited to, gender, age, genetic predisposition, environmental exposure, and lifestyle.

As used herein, the term "characterizing AMD in subject" refers to the identification of one or more properties of AMD in a subject (e.g. degree, severity, advancement, etc.). AMD may be characterized by the identification of one or more markers (e.g., SNPs and/or haplotypes) of the present invention.

As used herein, the term "reagent(s) capable of specifically detecting biomarker expression" refers to reagents used to detect the expression of biomarkers (e.g., SNPs and/or haplotypes described herein). Examples of suitable reagents include but are not limited to, nucleic acid probes capable of specifically hybridizing to mRNA or cDNA, and antibodies (e.g., monoclonal antibodies).

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "providing a prognosis" refers to providing information regarding the impact of the presence of AMD (e.g., as determined by the diagnostic methods of the present invention) on a subject's future health.

As used herein, the term "non-human animals" refers to all non-human animals including, but not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "transgene" refers to a heterologous gene that is integrated into the genome of an organism (e.g., a non-human animal) and that is transmitted to progeny of the organism during sexual reproduction.

As used herein, the term "transgenic organism" refers to an organism (e.g., a non-human animal) that has a transgene integrated into its genome and that transmits the transgene to its progeny during sexual reproduction.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 (1972)). Other nucleic acids will not be replicated by this amplification enzyme. Similarly, in the case of T7 RNA polymerase, this amplification enzyme has a stringent specificity for its own promoters (Chamberlin et al., Nature 228:227 (1970)). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press (1989)).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to the region of nucleic acid bounded by the primers. Thus, the "target" is sought to be sorted out from other nucleic acid sequences. A "segment" is defined as a region of nucleic acid within the target sequence.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., AMD). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include saliva, tissues, lacrimal fluid, and blood products, such as plasma, serum and the like. Environmental samples include environmental material such as surface matter, soil, water, and industrial samples. Such examples are not however to be construed as limiting the sample types applicable to the present invention.

DETAILED DESCRIPTION OF EMBODIMENTS

The present invention relates generally to biomarkers for macular degeneration. In particular, the present invention provides a plurality of biomarkers (e.g., polymorphisms and/or haplotypes) for monitoring and diagnosing macular degeneration. The compositions and methods of the present invention find use in diagnostic, therapeutic, research, and drug screening applications. The present invention further provides assay for identifying, characterizing, and testing therapeutic agents that find use in treating macular degeneration.

During development of embodiments of the present invention, a genomewide association scan was performed for age-related macular degeneration (AMD) in 2,157 cases and 1,150 controls. In addition to statistically validating loci near CFH, ARMS2, C2/CFB, C3 and CFI, association near TIMP3, a gene implicated in early-onset maculopathy, and LIPC, a gene involved in regulating high-density lipoprotein (HDL) levels, was identified. Consistent with the causal relationship between HDL metabolism and AMD, association was identified with alleles near CETP, LPL and ABCA1. Multi-locus analysis, including a panel of seven loci (CFH, ARMS2, C3, C2/CFB, CFI, TIMP3/SYN3 and LIPC), shows 329/331 individuals with the highest risk genotypes in sample are cases, 85% with advanced AMD. Experiments performed during development of embodiments of the present invention provide new insights into underlying biology and therapies for AMD.

Accordingly, in some embodiments, the present invention provides methods for detection of AMD, characterizing the severity and/or advancement of AMD, and/or diagnosing a subject's susceptibility for AMD. In some embodiments, the present invention detects the presence of one or more of the SNPs described herein. The present invention is not limited by the method utilized for detection. Indeed, a variety of different methods are known to those of skill in the art including, but not limited to, microarray detection, TAQMAN, PCR, allele specific PCR, sequencing, and other methods.

In some embodiments, the present invention provides indicators (e.g. alleles, loci, SNPs, halotypes, etc.) of increased susceptibility to AMD for an individual or population. In some embodiments, a single indicator (e.g. SNP) indicates an increased AMD-susceptibility. In some embodiments, a combination of any of the SNPs listed herein indicates heightened risk of AMD or developing AMD (e.g. 2 or more SNPs, 3 or more SNPs, 4 or more SNPs, 5 or more SNPs, 6 or more SNPs, 7 or more SNPs, 8 or more SNPs, 9 or more SNPs, etc.). In some embodiments, combinations of the SNPs listed herein indicates heightened risk of AMD or developing AMD. In some embodiments, specific combinations of the SNPs listed herein indicate increased risk of AMD or developing AMD. In some embodiments, combinations of SNPs listed herein indicate increased severity of AMD. In some embodiments, increased number of SNPs listed herein indicates increased severity of AMD (e.g. 2 or more SNPs, 3 or more SNPs, 4 or more SNPs, 5 or more SNPs, 6 or more SNPs, 7 or more SNPs, 8 or more SNPs, 9 or more SNPs, etc.). In some embodiments, specific combinations of SNPs listed herein indicates increased severity of AMD. In some embodiments, a greater number of SNPs which are indicative of AMD correlates to a greater risk of AMD for an individual or population. In some embodiments, combinations of the SNPs listed herein indicate protective effects (e.g. reduced severity of AMD, reduced risk of AMD, reduced cholesterol, etc.).

In some embodiments, the compositions, methods, or kits utilize markers, listed herein, alone in combination with each other or other markers of AMD. The following references provide additional markers of AMD which may find utility in embodiments of the present invention: Kanda et al. Proc Natl Acad Sci USA. 2007 Oct. 23; 104(43):16725-6, Edwards et al. N Engl J Med. 2009 May 21; 360(21):2254-5, Fisher et al. (2005) Hum Mol Genet 14:2257-2264, Swaroop et al. (2007) Hum Mol Genet 16 Spec No. 2:R174-182, Edwards A O, et al. (2005) Complement factor H polymorphism and age-related macular degeneration. Science 308:421-424, Hageman et al. (2005) *Proc Natl Acad Sci USA* 102:7227-7232, Haines et al. (2005) *Science* 308:419-421, Klein et al. (2005) *Science* 308: 385-389, Zareparsi et al. (2005) *Am J Hum Genet* 77:149-153, Clark et al. (2006) *J Biol Chem* 281:24713-24720, Hollyfield et al. (2008) *Nat Med* 14:194-198, Jakobsdottir et al. (2005) *Am J Hum Genet* 77:389-407, Rivera et al. (2005) *Hum Mol Genet* 14:3227-3236, Maller et al. (2006) *Nat Genet* 38:1055-1059, Schmidt et al. (2006) *Am J Hum Genet* 78:852-864, Kanda et al. (2007) *Proc Natl Acad Sci USA* 104:16227-16232, Fritsche et al. (2008) Age-related macular degeneration is associated with an unstable ARMS2 (LOC387715) mRNA. *Nat Genet*, U.S. Pat. No. 7,351,524, U.S. Pat. No. 7,344,846, U.S. Pat. No. 7,108,982, U.S. Pat. No. 7,011,952, US Pub. App. No. 20090124542, US Pub. App. No. 20080318264, US Pub. App. No. 20080280825, US Pub. App. No. 20080274453, US Pub. App. No.

20080261211, US Pub. App. No. 20080146501, US Pub. App. No. 20080131418, US Pub. App. No. 20070020647, US Pub. App. No. 20060263819, US Pub. App. No. 20050287601, US Pub. App. No. 20030017501, US Pub. App. No. 20020160954, US Pub. App. No. 20020102581, US Pub. App. No. 20020015957, U.S. Pat. No. 7,351,534, U.S. Pat. No. 7,309,487, U.S. Pat. No. 6,593,104, and U.S. Pat. No. 6,417,342 (herein incorporated by reference in their entireties).

In some embodiments, the present invention provides kits for the detection and characterization of AMD. In some embodiments, the kits contain reagents for detecting SNPs described herein and/or antibodies specific for AMD biomarkers, in addition to detection reagents and buffers. In other embodiments, the kits contain reagents specific for the detection of AMD biomarker mRNA, SNPs, cDNA (e.g., oligonucleotide probes or primers), etc. In preferred embodiments, the kits contain all of the components necessary to perform a detection assay, including all controls, directions for performing assays, and any necessary software for analysis and presentation of results. In some embodiments, kits comprise instructions (e.g. written, digital, and/or online) to perform assays for the detection and characterization of AMD.

In some embodiments, the expression of mRNA and/or proteins associated with SNPs of the present invention are determined. In some embodiments, the presence or absence of SNPs are correlated with mRNA and/or protein expression. In some embodiments, gene silencing (e.g., siRNA and/or RNAi) is utilized to alter expression of genes associated with SNPs described herein.

In some embodiments, the present invention contemplates screening arrays of compounds (e.g., pharmaceuticals, drugs, peptides, or other test compounds) for their ability to alter expression, activity, structure, and/or interaction with other proteins, to compensate for altered function of the genes and loci disclosed herein. In some embodiments, compounds (e.g., pharmaceuticals, drugs, peptides, or other test compounds) identified using screening assays of the present invention find use in the diagnosis or treatment of AMD.

In some embodiments, the present invention provides screening assays for assessing cellular behavior or function. For example, the response of cells, tissues, or organisms to interventions (e.g., drugs, diets, aging, etc.) may be monitored by assessing, for example, cellular functions using animal or cell culture models as describe herein. Such assays find particular use for characterizing, identifying, validating, selecting, optimizing, or monitoring the effects of agents (e.g., small molecule-, peptide-, antibody-, nucleic acid-based drugs, etc.) that find use in treating or preventing AMD or related diseases or conditions.

In some embodiments, the present invention provides methods for detection of expression of AMD markers (e.g., SNPs of CLH, ARMS2, CETP, etc.). In preferred embodiments, expression is measured directly (e.g., at the RNA or protein level). In some embodiments, expression is detected in vivo or in vitro. In some embodiments, expression is detected in tissue samples (e.g., biopsy tissue). In other embodiments, expression is detected in bodily fluids (e.g., including but not limited to, plasma, serum, whole blood, mucus, and urine). In some embodiments, the present invention provides methods of identifying or characterizing AMD, or response thereof to therapy, based on the level expression of markers listed herein (e.g., mRNA or transcript levels).

The present invention further provides panels and kits for the detection of markers. In preferred embodiments, the presence of AMD marker is used to provide a prognosis to a subject. The information provided is also used to direct the course of treatment. For example, if a subject is found to have a plurality of markers indicative of AMD, therapy or other interventions can be started at an earlier point when it is more likely to be effective. In some embodiments, assaying the presence or absence of AMD markers is performed after diagnosis of AMD, but prior to treatment. In some embodiments, assaying the presence or absence of AMD markers is performed after treatment of AMD.

The present invention is not limited to the markers described herein. Any suitable marker that correlates with AMD or AMD onset or progression may be utilized, including but not limited to, those described in the illustrative examples below. Additional markers are also contemplated to be within the scope of the present invention. Any suitable method may be utilized to identify and characterize AMD markers suitable for use in the methods of the present invention, including but not limited to, those described herein.

In some embodiments, the present invention provides a panel for the analysis of a plurality of markers. The panel allows for the simultaneous analysis of multiple markers correlating with AMD. For example, a panel may include markers identified as correlating with severity of AMD, onset of AMD, and/or risk of AMD, in a subject that is/are likely or not likely to respond to a given treatment. Depending on the subject, panels may be analyzed alone or in combination in order to provide the best possible diagnosis and prognosis. Markers for inclusion on a panel are selected by screening for their predictive value using any suitable method, including but not limited to, those described herein.

In some embodiments, AMD markers are detected by measuring the expression of corresponding mRNA in a tissue or other sample (e.g., a blood sample). mRNA expression may be measured by any suitable method, including but not limited to, those disclosed below.

DNA or RNA markers may be detected, for example, by hybridization to an oligonucleotide probe. A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

In other embodiments, gene expression of AMD disease markers is detected by measuring the expression of the corresponding protein or polypeptide. Protein expression may be detected by any suitable method. In some embodiments, proteins are detected by their binding to an antibody raised against the protein.

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of AMD to respond to a specific therapy) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or severity of disease.

In some embodiments, the present invention provides kits for the detection and characterization of AMD. In some embodiments, the kits contain reagents specific for an AMD marker, in addition to detection reagents and buffers. In other embodiments, the kits contain reagents specific for the detection of DNA or RNA (e.g., oligonucleotide probes or primers). For example, in some embodiments, the kits contain primers and reagents needed to perform PCR for detection and characterization of AMD. In some embodiments, the kits contain all of the components necessary to perform a detection assay, including all controls, directions for performing assays, and any necessary software for analysis and presentation of results.

In some embodiments, the present invention provides drug screening assays (e.g., to screen for drugs useful in treating AMD). The screening methods of the present invention utilize AMD markers identified using the methods of the present invention. For example, in some embodiments, the present invention provides methods of screening for compound that alter (e.g., increase or decrease) the expression of AMD marker genes. In some embodiments, candidate compounds are antisense agents (e.g., oligonucleotides) directed against AMD markers.

In some embodiments, alleles in linkage disequilibrium with AMD-associated SNPs affect expression or activity of downstream genes. In some embodiments, correction of these gene activities by increasing or decreasing the expression by gene-based vectors, RNAi, etc. is used for designing therapies.

This invention further pertains to novel agents identified by the screening assays described herein or other screening assays. Accordingly, it is within the scope of this invention to further use an agent identified as described herein (e.g., an AMD marker modulating agent, an antisense AMD marker nucleic acid molecule, a siRNA molecule, an AMD marker specific antibody, or an aAMD marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein.

In some embodiments, the present invention provides therapies for AMD. In some embodiments, therapies target AMD markers

EXPERIMENTAL

Example 1

Compositions and Methods for Genome-Wide Association Analysis

Samples in the genome-wide association study performed during development of embodiments of the present invention (Discovery Sample) were collected at the University of Michigan in Ann Arbor (coordinated by AS), the University of Pennsylvania in Philadelphia (coordinated by DS), and at the Mayo Clinic in Rochester, Minn. (coordinated by AE). Detailed information about the number of cases and controls and the distribution of age, gender and disease severity in each collection is summarized in Table 1. All cases and controls in the discovery sample were evaluated by an Ophthalmologist and/or had fundus grading performed by either a retina specialist or a retinal grading center.

TABLE 1

Summary description of discovery samples used in the genome-wide association and replication studies.

| | | | | Cases | | | Controls | | | |
|---|---|---|---|---|---|---|---|---|---|---|
| | N | Male (%) | Age (Average) | Large Drusen (%) | Geographic Atrophy (%) | Exudative Disease (%) | N | Male (%) | Age (Average) | Total |
| Discovery samples | | | | | | | | | | |
| Michigan | 786 | 36.9 | 79.8 | 14.2 | 21.6 | 64.2 | 516 | 41.5 | 76.6 | 1,302 |
| Pennsylvania | 396 | 40.4 | 75.7 | 42.7 | 26.3 | 31.0 | 201 | 45.3 | 76 | 597 |
| Mayo Clinic | 535 | 36.1 | 77.3 | 46.5 | 13.6 | 39.8 | 433 | 46.7 | 70.2 | 968 |
| AREDS | 440 | 41.0 | 80.8 | not genotyped | 26.8 | 73.2 | 0 | 0 | 0 | 440 |
| Total | 2,157 | 38.2 | 78.6 | 24.5 | 21.6 | 53.9 | 1,150 | 44.1 | 74.1 | 3,307 |
| Parallel Discovery Sample | | | | | | | | | | |
| Tufts/MGH† | 821 | 46.0 | 80.3 | not genotyped | 27.5 | 72.5 | 1,728 | 46 | 76 | 2,549 |
| Replication samples | | | | | | | | | | |
| Tufts/MGH II | 868 | 40.0 | 79.7 | not genotyped | 28.3 | 71.7 | 789 | 40.0 | 73.0 | 1,657 |
| Johns Hopkins* | 665 | 32.8 | 75.5 | 21.8* | 12.4 | 57.2 | 131 | 31.3 | 74.7 | 796 |
| Pittsburgh* | 1,308 | 36.7 | 69.9 | 9.7* | 18.9 | 70.0 | 229 | 49.8 | 76.7 | 1,537 |
| Miami/Vanderbilt | 1,157 | 35.1 | 75.7 | 28.3 | 13.6 | 58.2 | 514 | 40.5 | 68.4 | 1671 |
| Oregon | 515 | 34.0 | 79.8 | not genotyped | 27.2 | 72.8 | 263 | 45.0 | 74.0 | 778 |
| Penn-NJ | 556 | 39.8 | 79.8 | 19.1 | 6.8 | 65.5 | 347 | 47.0 | 75.6 | 903 |
| Total | 5,069 | 36.4 | 75.7 | 13.9 | 17.9 | 65.7 | 2,273 | 42.2 | 72.9 | 7,342 |
| Grand Total* | 8,047 | 37.9 | 76.9 | 15.3* | 19.8 | 63.2 | 5,151 | 43.9 | 74.2 | 13,198 |

Samples that present with both primary geographic atrophy and exudative disease have been classified as exudative in the table above.
*Proportions of cases with large drusen, geographic atrophy, and exudative disease do not add up to 100.0% because 8.6% of case samples from Johns Hopkins and 0.4% of samples from Pittsburgh had intermediate drusen.
†The Tufts/MGH samples used here exclude 158 samples that overlap between the two studies.
N = number.

Genotyping was performed using Illumina Human370 Bead Chips (Illumina, San Diego, Calif., USA) and the Illumina Infinium II assay protocol (Gunderson et al. Methods in Enzymology 410, 359-376 (2006), herein incorporated by reference in its entirety). Allele cluster definitions for each single nucleotide polymorphism (SNP) were determined using Illumina BeadStudio Genotyping Module version 3.2.32 and the combined intensity data from 99% of the samples; the resulting cluster definitions were then used on all samples. Genotypes were not called if the quality threshold (gencall score) was below 0.25. Genotypes were not released from CIDR for SNPs which failed technical filters for call rates less than 85%, more than 1 HapMap replicate error, more than a 4% (autosomal) or 5% (X chromosome) difference in call rate between genders, more than 0.5% male AB frequency for X chromosome. Y and XY SNPs were manually reviewed and clusters adjusted or genotypes dropped as appropriate. Genotypes were released from CIDR for 344,942 (99.46%) of the attempted SNPs. Blind duplicate reproducibility was 99.992%.

To expand the genome coverage, a genome-wide imputation was performed using haplotypes from the HapMap CEU samples as templates. Imputation was performed using MACH (Yun Li, www dot sph dot umich dot edu slash csg slash abecasis slash Mach slash). For downstream analyses, poorly imputed SNPs were filtered out and focused on markers with estimated r2 between imputed and true genotypes >0.3.

EIGENSTAT software was used to adjust for modest population stratification. After adjustment for the first two principal components of ancestry, the genomic control parameter was 1.007.

To investigate the association between each genotyped or imputed SNP and AMD, a logistic regression was performed for each SNP assuming the additive model and adjusting for the top two eigenvectors from EIGENSTRAT. A total of seven independently associated SNPs in previously reported loci (CFH, ARMS2, C3, C2/CFB, CFI) were identified. These SNPs were included as covariates in logistic regression analyses designed to identify additional loci associated with AMD.

To combine the statistics across different groups for replication, an arbitrary reference allele was selected for each marker and then calculated a z-statistic summarizing the evidence for association in each study (summarizing both the p-value, in its magnitude, and the direction of effect, in its sign). An overall z-statistic was calculated as a weighted average of the individual statistics and calculated the corresponding p-value. Weights were proportional to the square root of the number of individuals examined in each study and were selected such that the squared weights sum up to 1.0.

For samples including unrelated individuals only (all discovery samples, the Tufts/MGH samples and the Johns Hopkins, Oregon and Penn-NJ sample sets) the data were analyzed using simple logistic regression models with age and sex as covariates. For the discovery samples, the first two principal components of ancestry were used as covariates in all reported analyses and genotypes for the markers listed in Table 2 were used as covariates in a subset of the analyses (described in the text). For follow-up samples, genotypes at CFH and ARMS2 were included as covariates where available. For samples including related individuals, the data were analyzed (Thornton & McPeek. Am J Hum Genet 81, 321-37 (2007), herein incorporated by reference in its entirety).

TABLE 2

Confirmation of previously reported association signals in discovery sample.

| SNP | Chrom. | Position (basepair) | Notable Nearby Genes | Alleles (risk/non-risk) | Frequency (risk allele) Cases | Controls | OR | p-value | $\lambda_{sib}$ |
|---|---|---|---|---|---|---|---|---|---|
| *Primary Association Signals* | | | | | | | | | |
| rs10737680 | 1 | 194,946,078 | CFH | A/C | 0.801 | 0.566 | 3.11 | $1.62 \times 10^{-76}$ | 1.24 |
| rs3793917 | 10 | 124,209,265 | ARMS2/HTRA1 | G/C | 0.371 | 0.164 | 3.40 | $4.08 \times 10^{-60}$ | 1.45 |
| rs429608 | 6 | 32,038,441 | C2/CFB | G/A | 0.92 | 0.842 | 2.16 | $2.46 \times 10^{-21}$ | 1.05 |
| rs2230199 | 19 | 6,669,387 | C3 | C/G | 0.224 | 0.163 | 1.74 | $1.04 \times 10^{-10}$ | 1.06 |
| rs2285714 | 4 | 110,858,259 | CFI | T/C | 0.464 | 0.395 | 1.31 | $3.38 \times 10^{-7}$ | 1.02 |
| *Secondary Association Signals* | | | | | | | | | |
| rs1329424 | 1 | 194,912,799 | CFH | T/G | 0.603 | 0.351 | 1.88 | $6.35 \times 10^{-16}$ | 1.11 |
| rs9380272 | 6 | 32,013,989 | C2/CFB | A/G | 0.016 | 0.012 | 4.31 | $2.31 \times 10^{-8}$ | 1.12 |

The table reports the sites of strongest association at previously reported loci. For two of these loci (near CFH and C2/CFB), we found evidence of independent secondary signals that remained significant even after adjusting for the strongest available signal, consistent with previous reports. Excluding imputed SNPs, we found evidence for independent disease alleles at CFH, C2/CFB and ARMS2; the two selected ARMS2 SNPs are imperfect proxies for the imputed SNP rs3793917.
P-values and odds ratios (OR) were calculated using a logistic regression model that also includes the first two principal components of ancestry, age and sex as covariates. The OR quantifies the increase risk conferred by a given risk allele for an individual subject having AMD in the study. The recurrence risk ratio $\lambda_{sib}$ quantifies the increase in risk to siblings of affected individuals attributable to a specific allele; the quantity is a simple function of allele frequencies and genotype specific prevalences[30]. For example, a $\lambda_{sib}$ of 1.24 implies that alleles at the first locus are responsible for 24% increase in risk to siblings of AMD patients compared to the general population.

TABLE 3

Novel Loci with Confirmed Association to AMD

| SNP | Chrom. | Position (basepair) | Notable Nearby Genes | Alleles (risk/non-risk) | Frequency (risk allele) Cases | Controls | OR | p-value | $\lambda_{sib}$ |
|---|---|---|---|---|---|---|---|---|---|
| rs9621532 | 22 | 31,414,511 | SYN3/TIMP3 | A/C | | | | | |
| Discovery sample (2,157 cases, 1,150 controls)... | | | | | 0.964 | 0.943 | 1.81 | $4.4 \times 10^{-5}$ | 1.011 |
| Tufts/MGH sample (821 cases, 1,728 controls)... | | | | | 0.959 | 0.947 | 1.40 | 0.017* | 1.013 |
| De novo replication sample (5,069 cases, 2,273 controls)... | | | | | 0.963 | 0.941 | 1.56 | $4.6 \times 10^{-6}$ | 1.006 |
| Combined sample (8,047 cases, 5,151 controls)... | | | | | 0.963 | 0.943 | 1.59 | $4.7 \times 10^{-11}$ | 1.007 |
| rs493258 | 15 | 56,475,172 | LIPC | C/T | | | | | |
| Discovery sample (2,157 cases, 1,150 controls)... | | | | | 0.564 | 0.528 | 1.21 | $2.1 \times 10^{-3}$ | 1.009 |
| Tufts/MGH sample (821 cases, 1,728 controls)... | | | | | 0.579 | 0.524 | 1.27 | $5.7 \times 10^{-4}$* | 1.013 |
| De novo replication sample (5,069 cases, 2,273 controls)... | | | | | 0.564 | 0.539 | 1.12 | 0.0019 | 1.003 |
| Combined sample (8,047 cases, 5,151 controls)... | | | | | 0.566 | 0.532 | 1.17 | $4.4 \times 10^{-8}$ | 1.007 |

This table summarizes regions of confirmed association (overall $p < 5 \times 10^{-8}$; corresponding to an adjustment for ~1 million independent tests). Follow-up analysis of top signals proceeded in a staged fashion. First, we imputed missing genotypes using the HapMap CEU reference panel. Next, we exchanged results for SNPs that were also present on the Affymetrix 6.0 chip and with evidence of association at $p < .001$ in an initial analysis with authors of an independent genome-wide association study (Tufts/MGH; see accompanying manuscript). Finally, we selected a set of SNPs for follow-up genotyping in additional samples. Each replication sample genotyped 10-30 SNPs with the exact number of SNPs determined according to resources available to each group. All loci with $p < 5 \times 10^{-8}$ in the combined analysis of all available data are listed above.
*The Tufts/MGH results reported above exclude 158 subjects that overlap between the two studies. Before excluding these overlapping samples, the Tufts/MGH association p-values were 0.019 at rs9621532 and $4.5 \times 10^{-5}$ at rs493258, respectively.

A simple logistic regression model to the data to evaluate the cumulative contribution of the alleles identified here to disease risk. The effect of each genotype was modeled on a log-additive scale, with no interaction terms between genotypes. Genotypes were sorted according to their fitted probability of disease and organized individuals into deciles of fitted risk. The proportion of affected individuals in each risk decile were counted. In a subsequent analysis, different weights to cases and controls were assigned, designed to reflect the fact that cases are enriched in the sample. Cases were assigned weight $f_{case}/p_{case}$ case and controls were assigned weight $f_{control}/p_{control}$, where $p_{case}$=0.65 and $p_{control}$=0.35 are the fractions of cases and controls in our sample and $f_{case}$=0.20 and $f_{control}$=0.80 are the expected fractions of cases and controls in an elderly population at age ~75. Taking these weights into account, the sample was divided into deciles ensuring that the summed weights in each decile were identical.

Example 2

Genome-Wide Association Analysis

Figure 2:
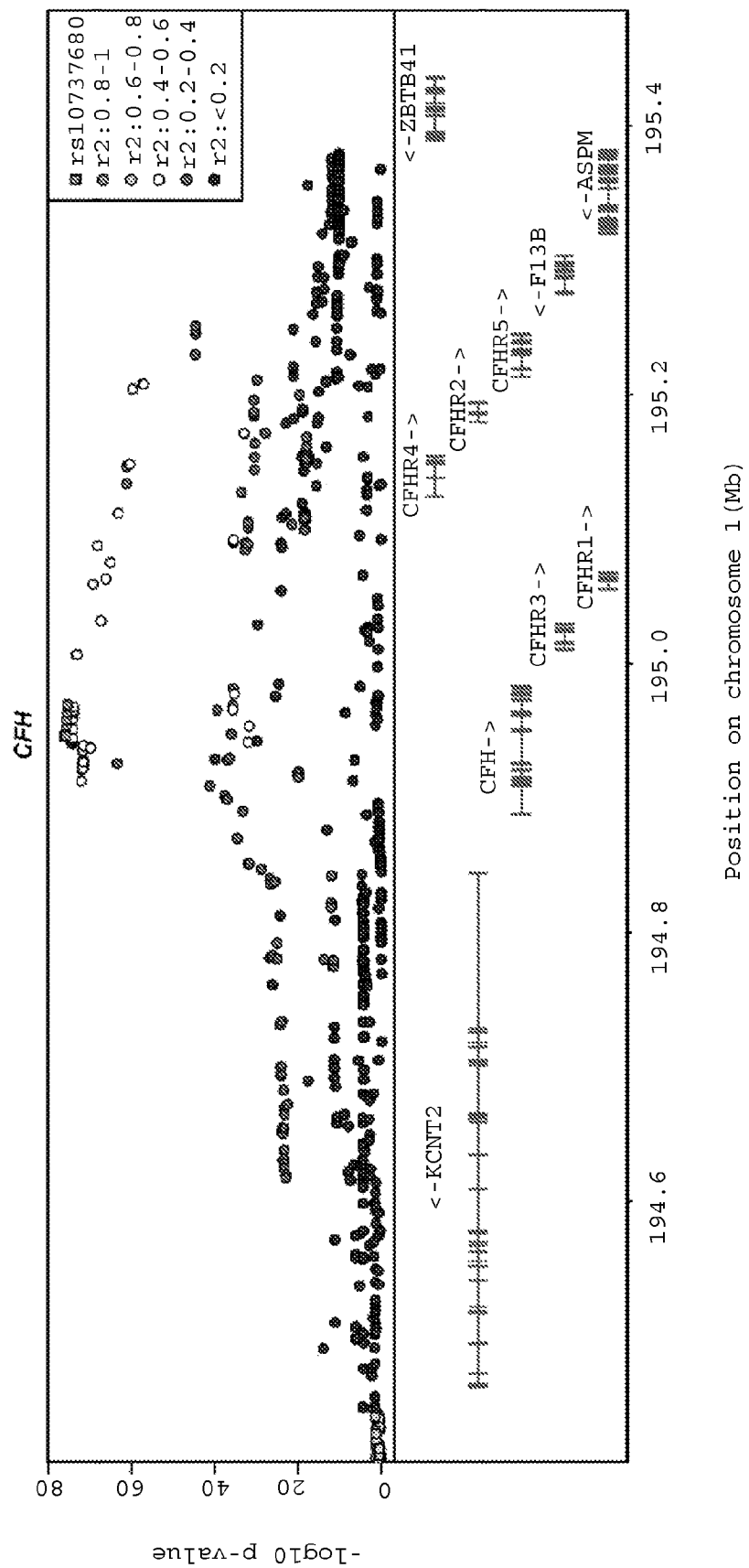
FIG. 2 shows regional plots for association signals in five previously reported loci: detailed plots of association in the discovery samples in five confirmed regions (CFH, ARMS, C2/CFB, C3 and CFI) are shown; the most significant SNP in each region is highlighted in a red square and other SNPs are drawn as colored circles reflecting linkage disequilibrium (LD) estimated from HapMap data set with the top selected SNP; the genes in each region are plotted below with position of exons and direction of transcription indicated.
Figure 2:
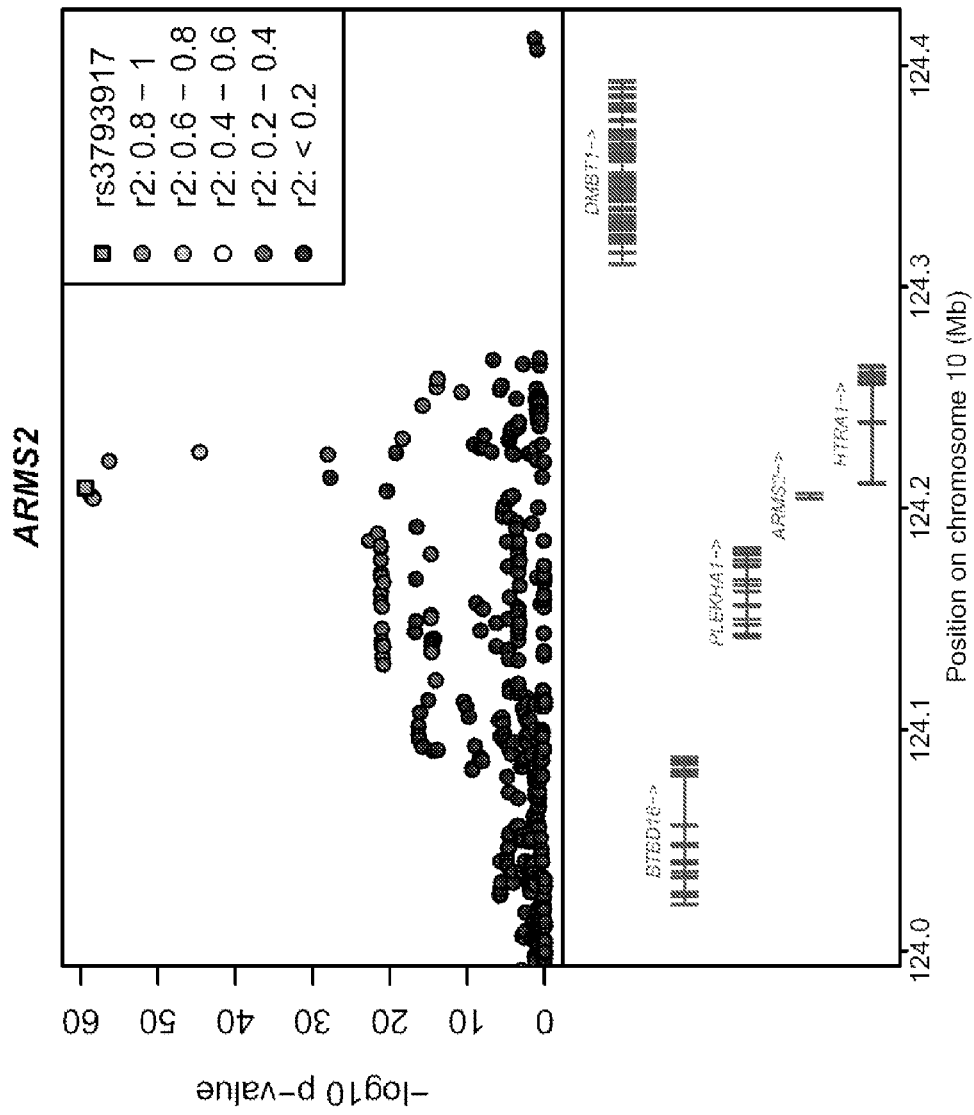
Figure 2:
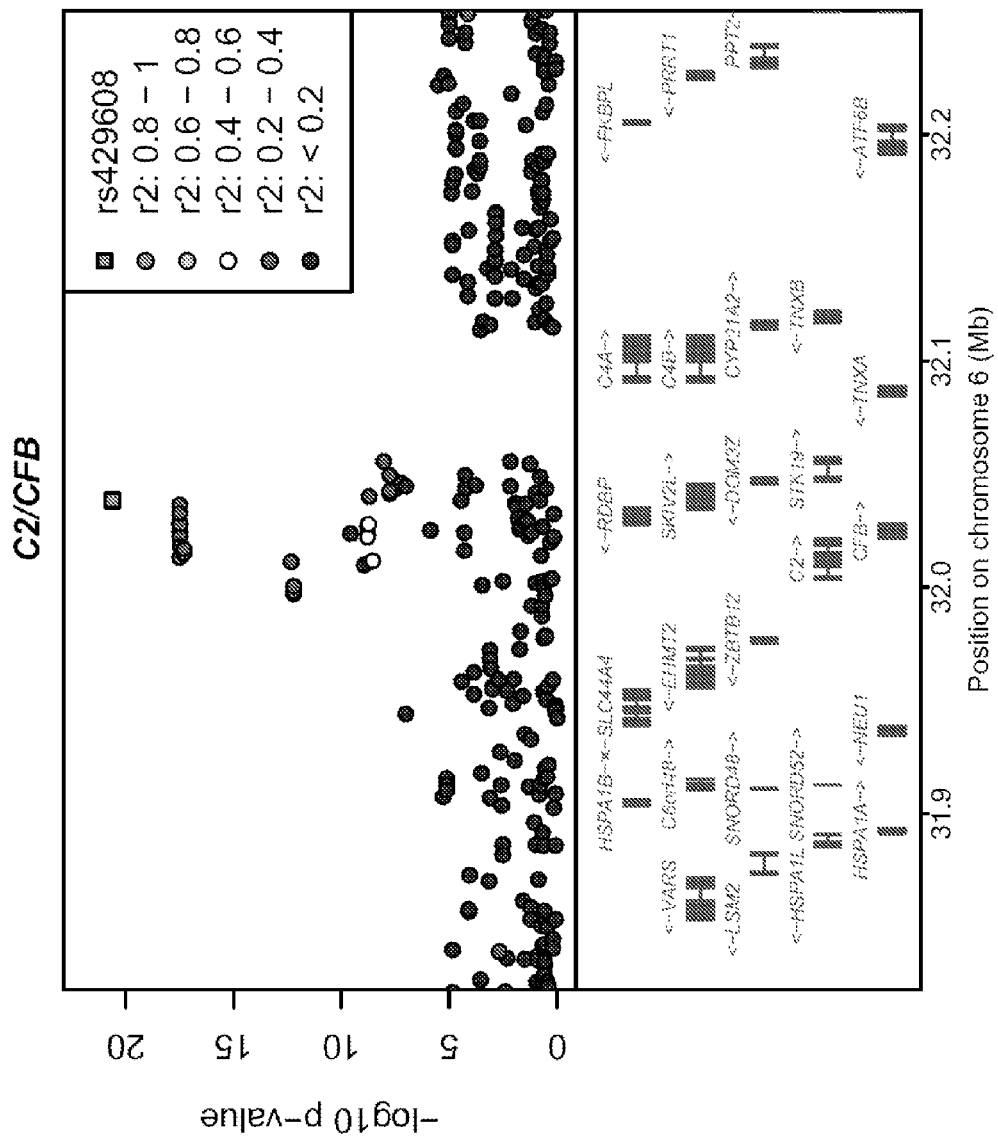
Figure 2:
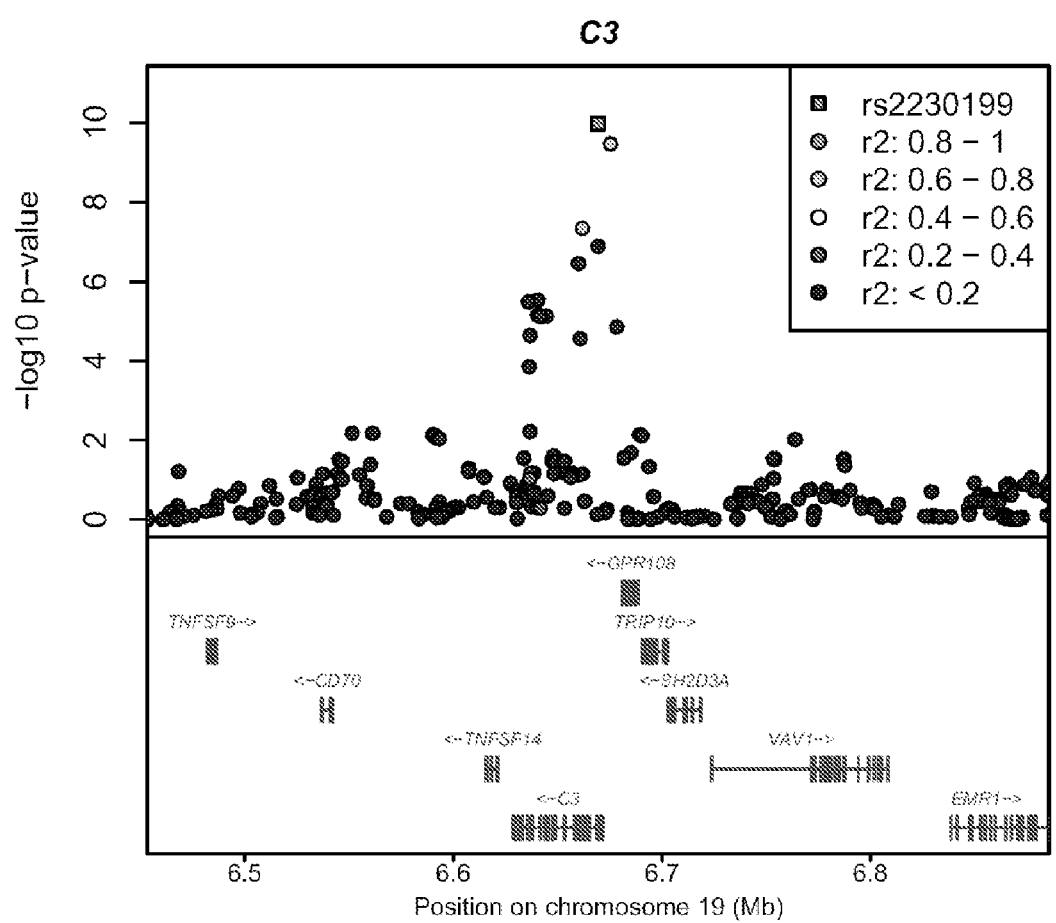
Figure 2:
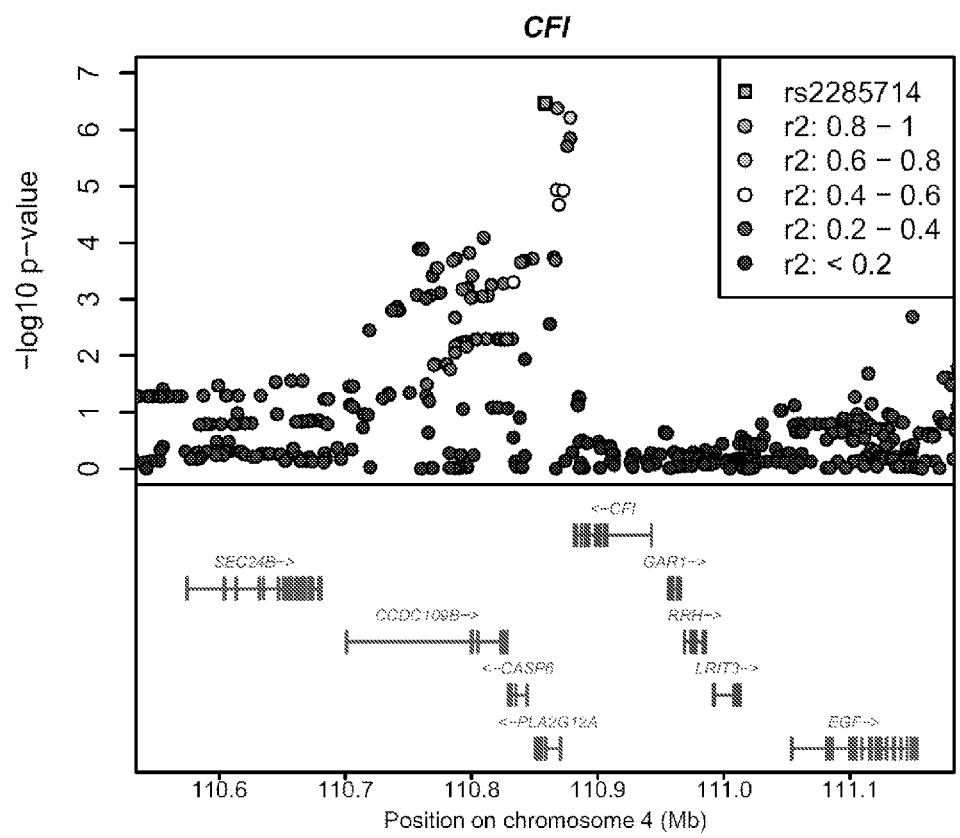

Study samples, including 75 blind duplicates, were genotyped together with HapMap controls at the Center for Inherited Disease Research using Illumina HumanHap 370 Infinium chips (Gunderson et al. Methods in Enzymology 410, 359-376 (2006), herein incorporated by reference in its entirety). Stringent quality control filters were used to ensure integrity of the dataset. Individuals with an unexpected first or second degree relative in the sample or with unusually low heterozygosity were excluded from analyses. Individuals with unexpectedly low genotyping completeness were checked for distinct genetic ancestry using principal components analysis (Price et al. Nat Genet 38, 904-9 (2006), herein incorporated by reference in its entirety). Markers with <95% call rate, minor allele frequency <1%, or evidence for deviation from Hardy-Weinberg equilibrium at p<10−6, were excluded. The average call rate for analyzed markers and samples was 99.94%. Short stretches of haplotype shared between individuals in the sample and those in the HapMap CEU28 were identified and used these to impute missing genotypes (Li et al. Annu Rev Genomics Hum Genet (in press) (2009), herein incorporated by reference in its entirety), An initial comparison of allele frequencies between cases and controls resulted in a genomic control parameter (Devlin & Roeder. Biometrics 55, 997-1004 (1999), herein incorporated by reference in its entirety) of 1.056; adjustment for the first two principal components of ancestry (Price et al. Nat Genet 38, 904-9 (2006), herein incorporated by reference in its entirety) reduced this to 1.007. Strong evidence of association was observed at established susceptibility loci (SEE Table 2, FIGS. 1 and 2); near CFH (strongest association at rs10737680, odds ratio 3.11, with $p<10^{-75}$), near ARMS2 (at rs3793917, OR=3.40, $p<10^{-59}$), near complement component 2 (C2) and complement factor B (CFB) genes (at rs429608, OR=2.16, $p<10^{-20}$), and near complement component 3 (C3) (at rs2230199, OR=1.74, $p=1\times10^{-10}$). Experiments performed during development of the present invention provide the first confirmation of the association between AMD and the complement factor I (CFI) locus (at rs2285714, OR=1.31, $p=3\times10^{-7}$). Conditioning on the strongest associated variant at each of these loci identified additional, strong association signals near CFH (at rs1329424, $p<10^{-15}$) and in the C2/CFB locus (at rs9380272, $p=2\times10^{-8}$), consistent with previous reports of multiple disease-associated alleles at these two loci1 (Jager et al. N Engl J Med 358, 2606-17 (2008), Li et al. Nat Genet 38, 1049-54 (2006), Maller et al. Nat Genet 38, 1055-9 (2006), herein incorporated by reference in their entireties). No evidence of association at several previously suggested susceptibility loci was obtained (SEE Table 4). A series of additional analyses were performed to identify new AMD susceptibility loci. Conditioned on the seven strongly associated SNPs (SEE Table 2), the analysis was repeated. No single SNP was significant at $p<5\times10^{-8}$ in this conditional analysis. Initial results were exchanged with the Tufts Medical Center/Massachusetts General Hospital (Tufts/MGH) genome-wide association study (Neale et al. Nature Genetics submitted (2009), herein incorporated by reference in its entirety) for SNPs that could be assayed directly with Affymetrix 6.0 genotyping arrays and that were significant at p<0.001. After excluding a small number of samples that were genotyped in both studies, SNPs were examined in additional cases with geographic atrophy or neovascularization and controls from the Tufts/MGH study. Twenty-five SNPs showing consistent evidence of association in both samples and five other SNPs with strong evidence for association but with no suitable Affymetrix 6.0 surrogate were selected for follow-up genotyping in additional cases and controls. A summary description of replication samples is included in Table 1.

TABLE 4

Association results of published candidate SNPs

| Gene | SNP | RiskAllele/Other | Pvalue0 | Reference | Pvalue1 | Pvalue2 | Direction |
|---|---|---|---|---|---|---|---|
| TLR3 | rs3775291 | C/T | 1.24E−07 | Yang Z et al. NEJM 2008 | 0.53 | 0.89 | opposite |
| TLR4 | rs4986790 | G/A | 0.001 | Zareparsi S et al. HMG 2005 | 0.55 | 0.09 | same |
| SERPING1 | rs2511989 | G/A | 7.49E−08 | Ennis S et al. Lancet 2008 | 0.94 | 0.92 | same |
| ERCC6 | rs3793784 | G/C | 0.02 | Tuo J et al. PNAS 2005 | 0.96 | 0.48 | same |
| LRP6 | rs7294695 | C/G | 0.02 | Haines JL et al. IOVS 2006 | 0.54 | 0.87 | same |
| CX3CR1 | rs3732378 | A/G | 0.002 | Tuo J et al. FASEB J. 2004 | 0.15 | 0.10 | same |

There is no strong evidence to support the genes TLR3, TLR4, SERPING1, ERCC6, LRP6 previously reported in the literature. Other reported genes VLDLR, ABCA4, VEGF and IL8 are not listed in the table since the reported SNPs are not in our data. None of the SNPs in our data show significance after adjusting for multiple testing in the region of those genes.
Pvalue0 is the reported pvalue in the literature.
Pvalue1 is the unconditional pvalue in our scan.
Pvalue2 is the pvalue conditional on known loci in our scan.

Figure 3:
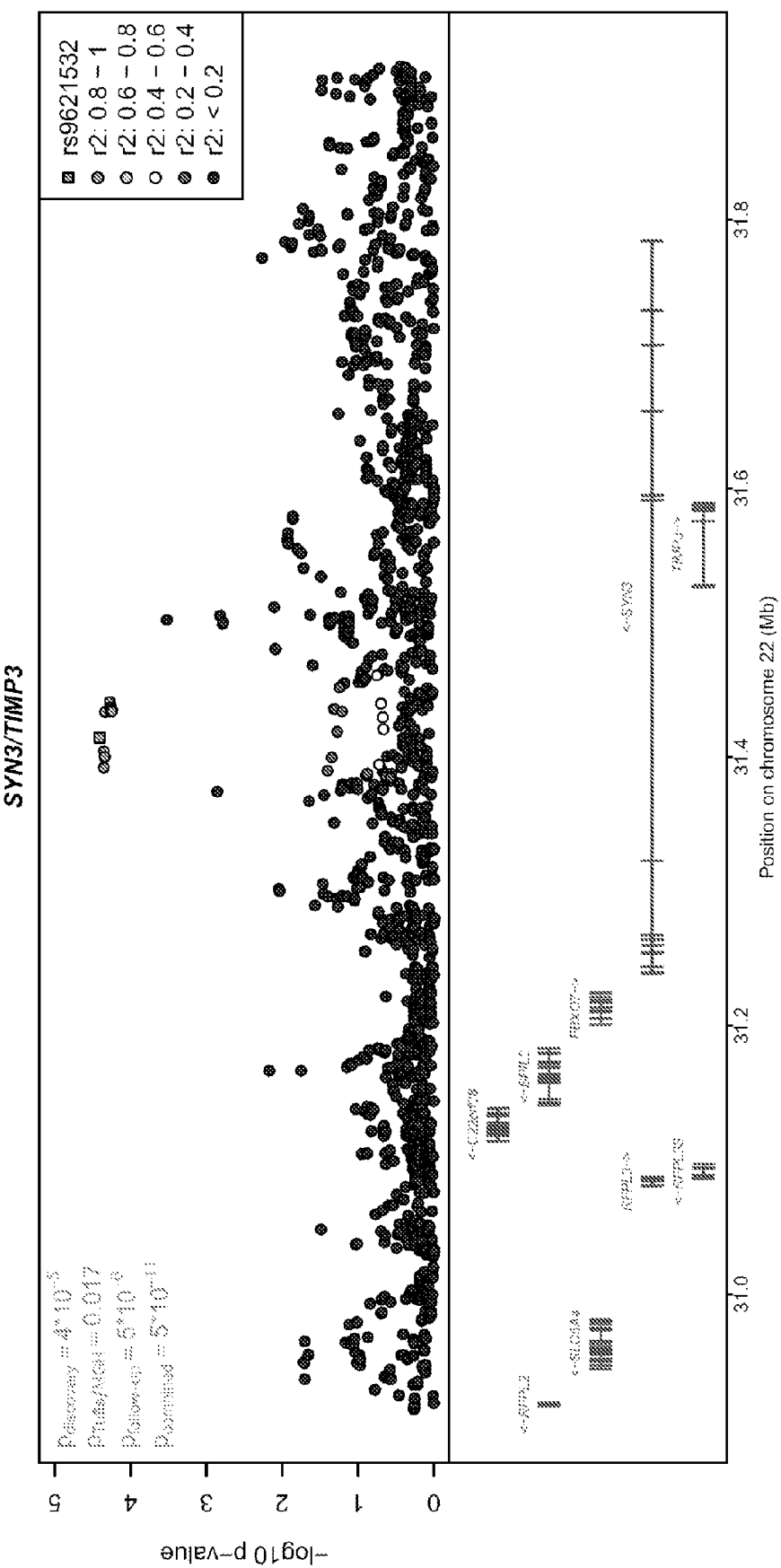
FIG. 3 shows detailed plots of novel association signals for the regions surrounding the SYN3/TIMP3 and LIPC regions; original, follow-up, and combined p-values for the SNP selected for replication are indicated on the left; discovery sample p-values for the index SNP and other nearby SNPs are plotted.
Figure 3:
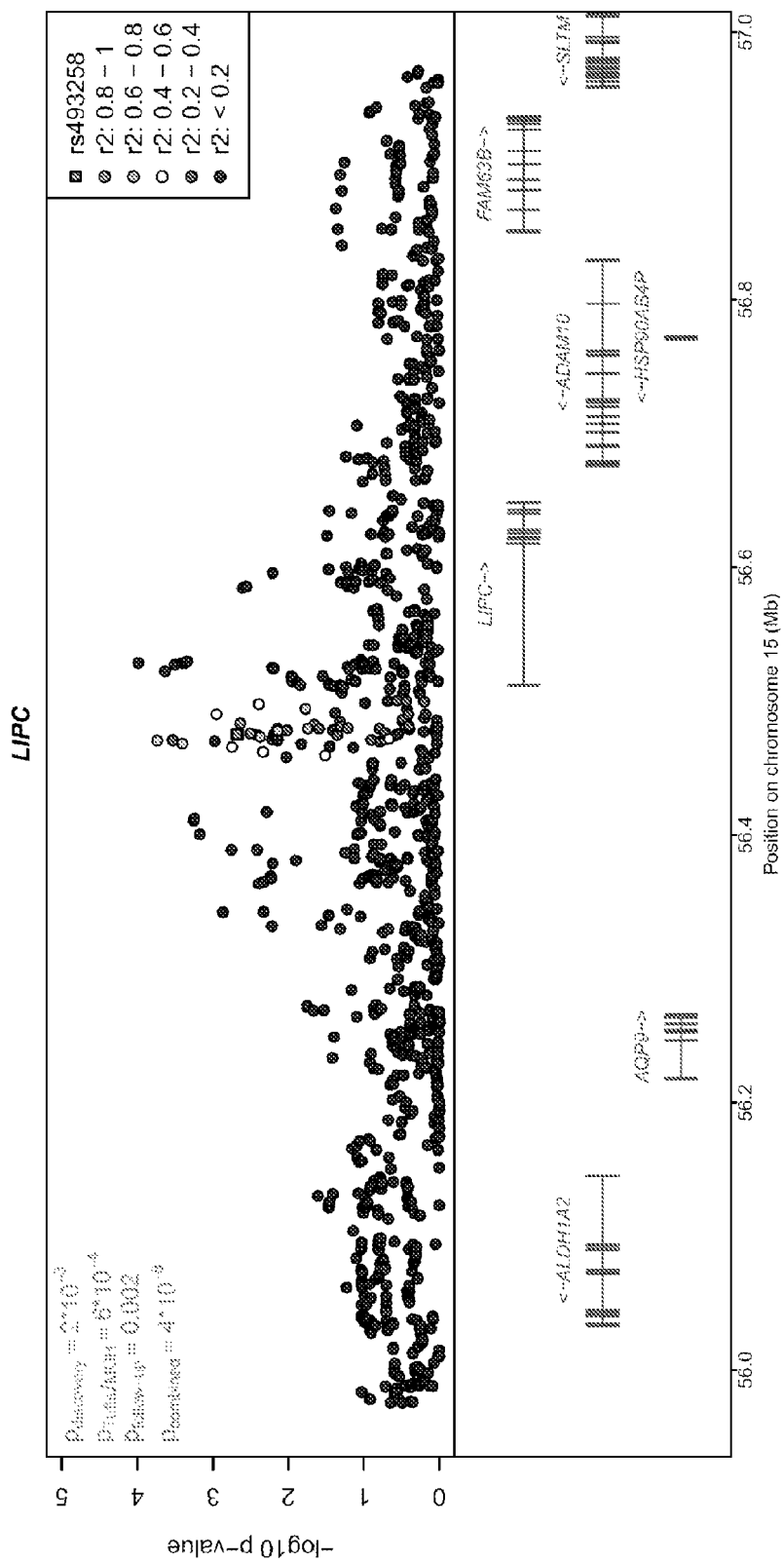

The additional analyses resulted in evidence of association signals at two new loci (SEE FIG. 3 and Table 3). At one locus, near TIMP3 (within an intron of SYN3) on chromosome 22, very common alleles (frequency of ~0.94 in controls) at rs9621532 and nearby markers were associated with increased risk of AMD (OR=1.59, $p=4.7\times10^{-11}$). Near LIPC on chromosome 15, the common allele at rs493258 (frequency of ~0.53 in controls) was also associated with increased risk of AMD (OR=1.17, $p=4.4\times10^{-8}$). Whereas strong evidence of association with rs9621532 near TIMP3 was observed in the initial scan, initial evidence of association at rs493258 near LIPC came from the Tufts/MGH genome-wide scan (p=4.5×10−5 in their discovery sample). The signals suggest new biological pathways for genes influencing disease susceptibility.

The first signal (SNP rs9621532), on chromosome 22, maps to a large intron of the synapsin III (SYN3) gene, encoding a neuron specific protein that plays critical roles in neurotransmission and synapse formation (Feng et al. J Neurosci 22, 4372-80 (2002). herein incorporated by reference in its entirety). The SNP is located in a 116-bp region that is highly conserved across vertebrates and ~100 kb upstream of TIMP3, an inhibitor of metalloproteinase 3 encoded within the same intron of SYN3. TIMP3 is involved in degradation of the extracellular matrix and mutated in Sorbys Fundus Dystrophy (Weber et al. Nat Genet 8, 352-6 (1994), herein incorporated by reference in its entirety), an early onset macular degenerative disease that shares clinical features with AMD. Linkage of AMD to the region has been reported previously (Abecasis et al. Am J Hum Genet 74, 482-94 (2004), herein incorporated by reference in its entirety), suggesting that the locus also harbors rare high penetrance alleles.

The second AMD-associated signal (SNP rs493258), upstream of hepatic lipase (LIPC) gene on chromosome 15q22, has been associated previously with HDL-cholesterol levels in blood (Willer et al. Nature Genetics 40, 161-9

Figure 4:
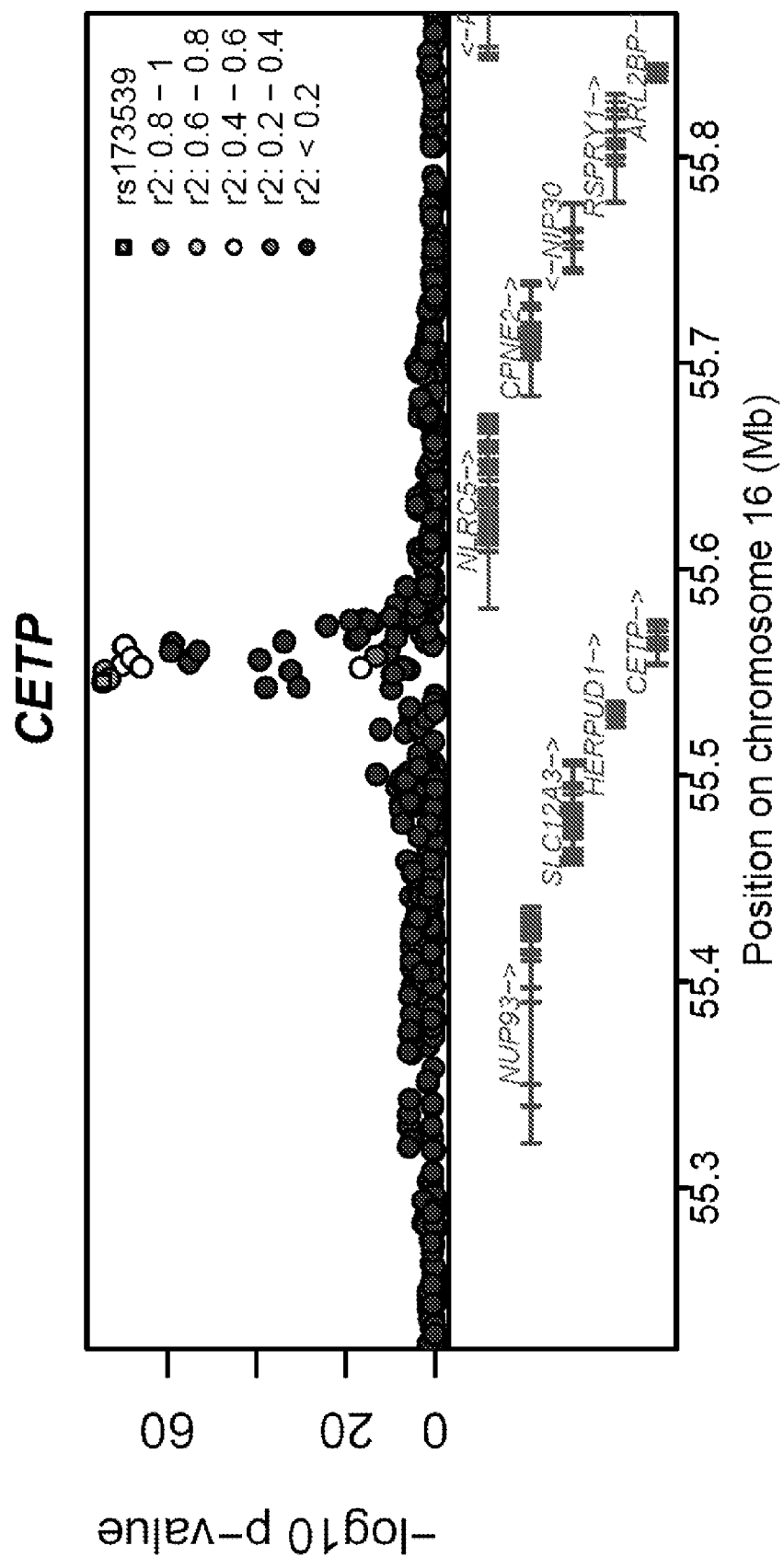
FIG. 4 shows detailed plots comparing HDL-cholesterol association signals and AMD association signals; the same marker and linkage disequilibrium proxies are highlighted in each row.
Figure 4:
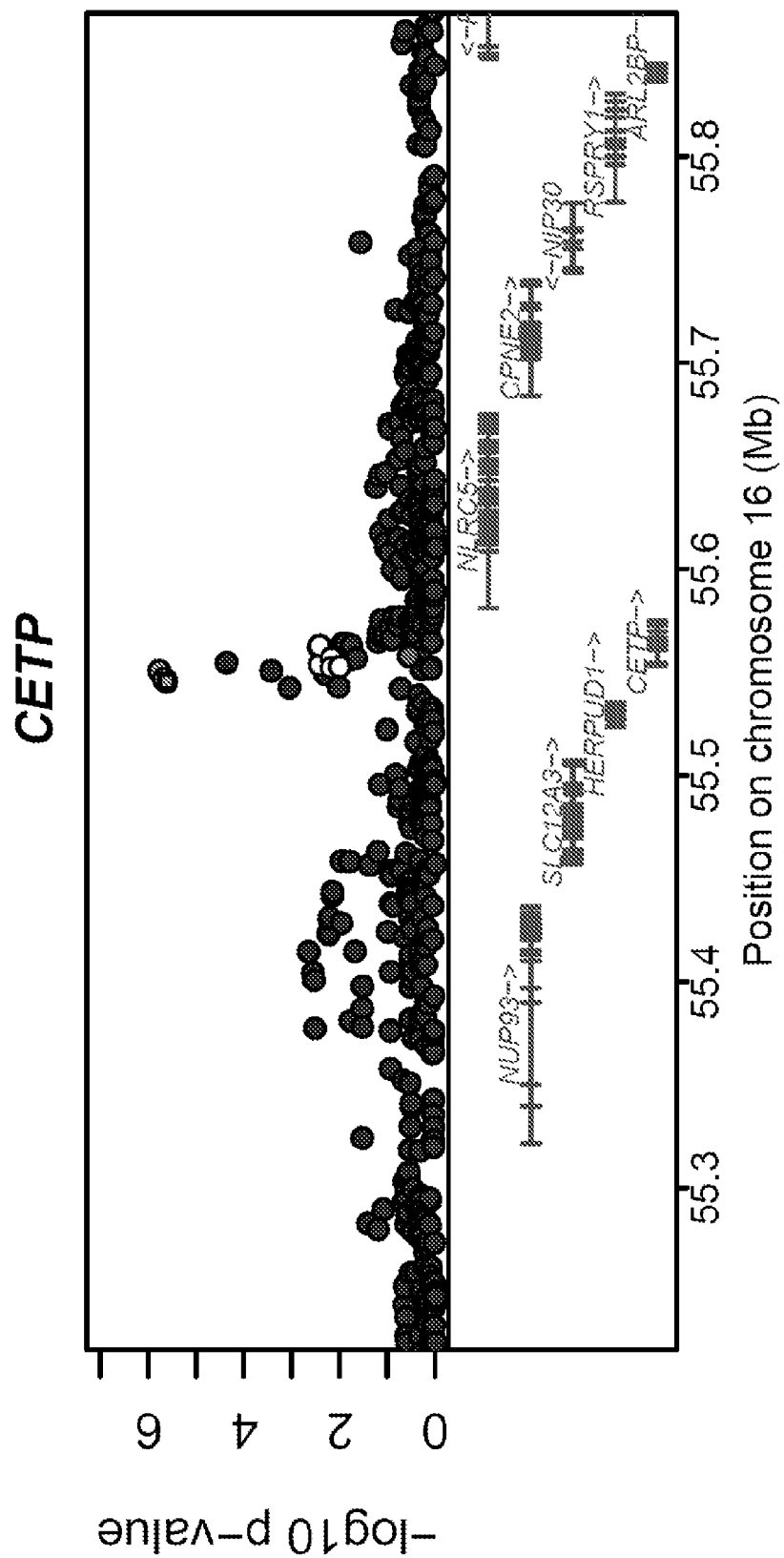
Figure 4:
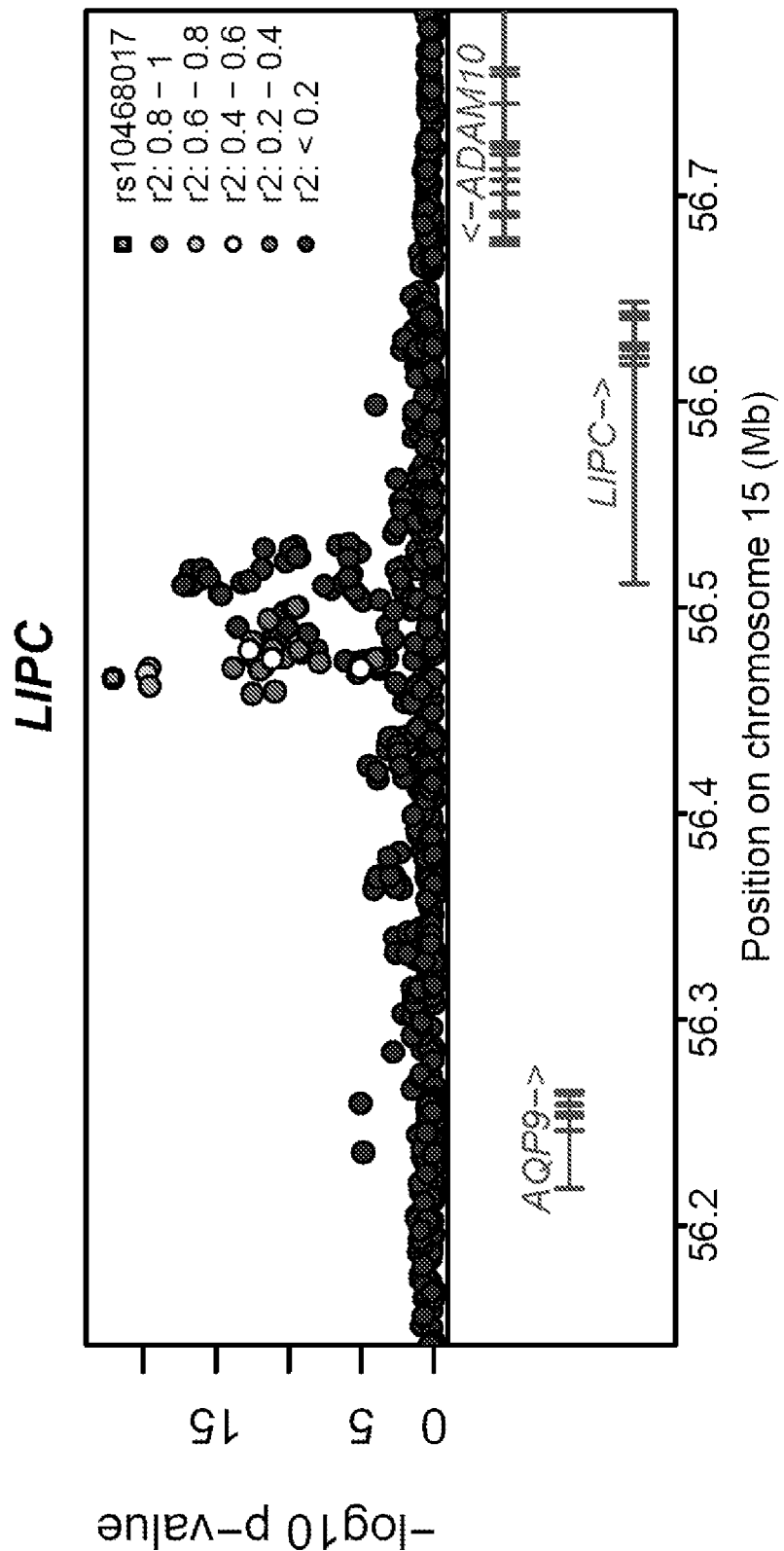
Figure 4:
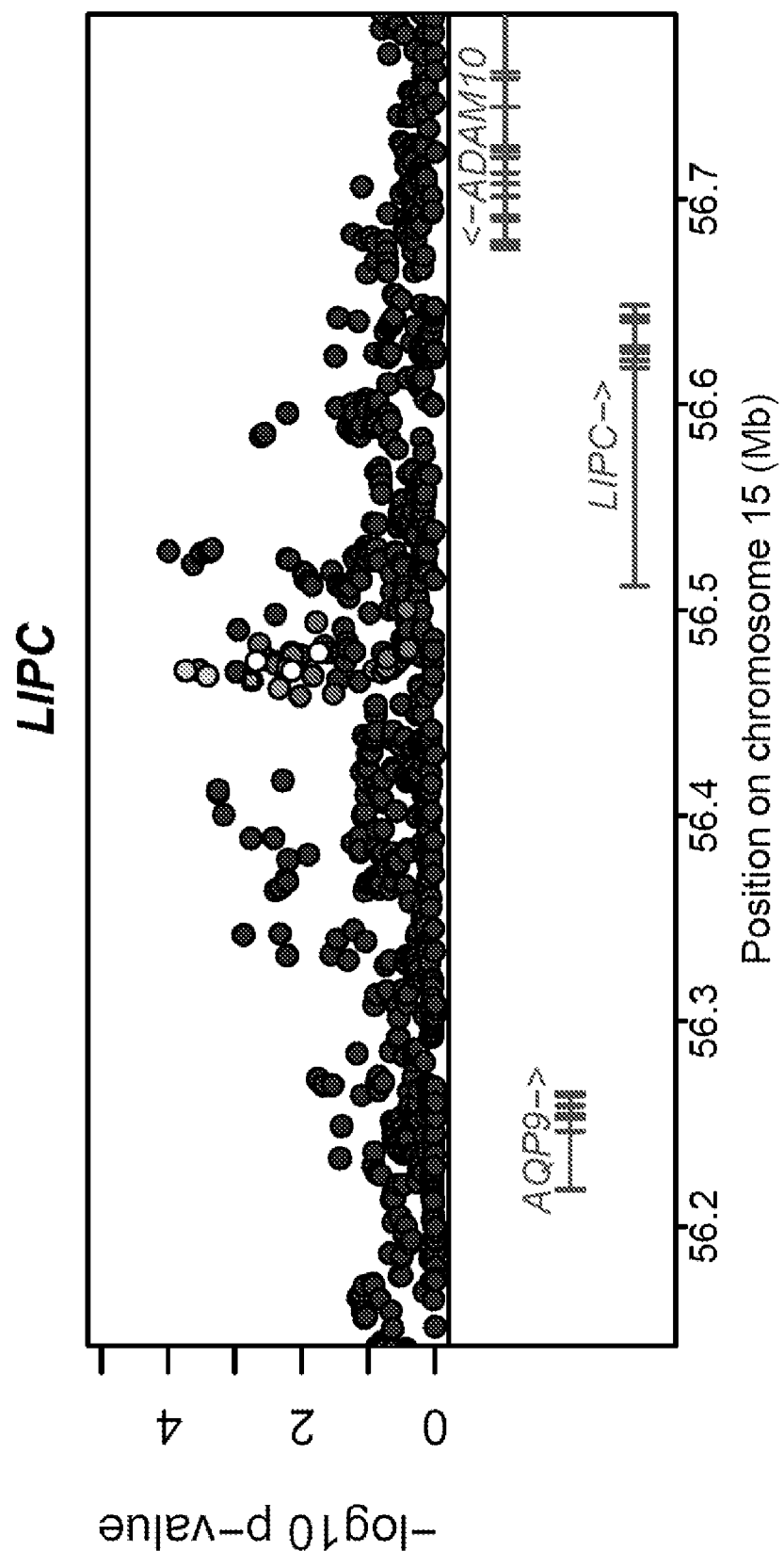
Figure 4:
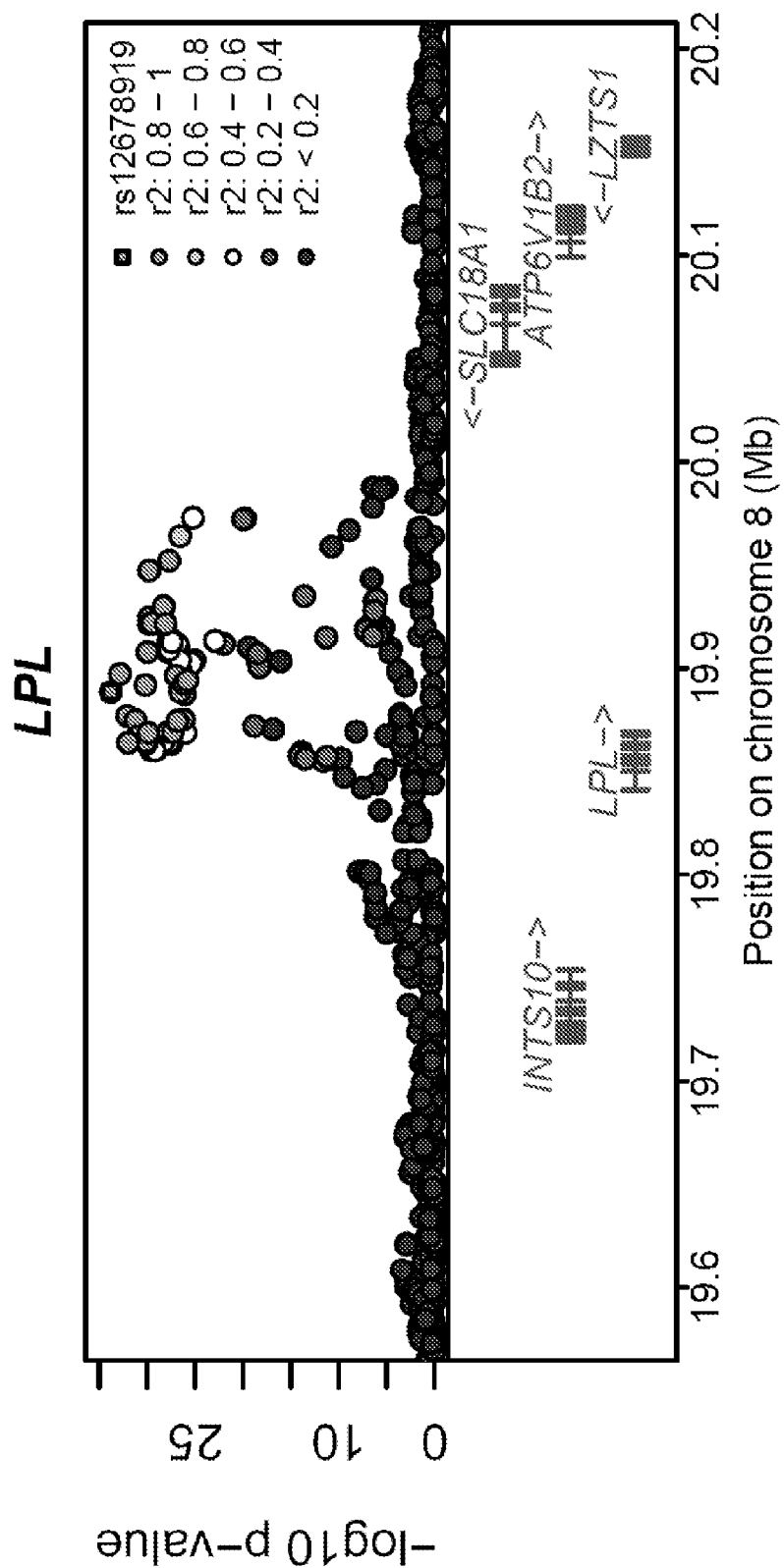
Figure 4:
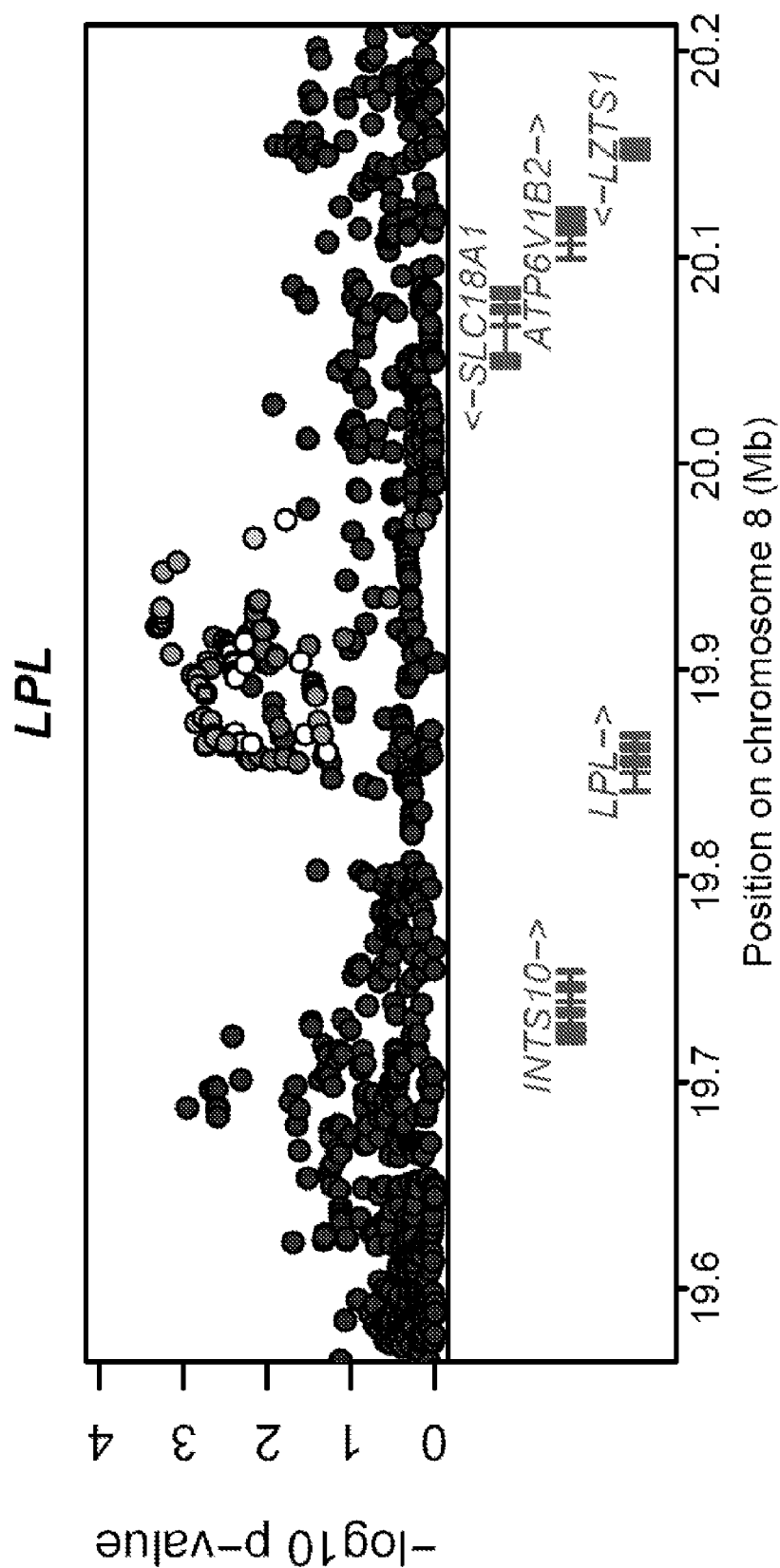
Figure 4:
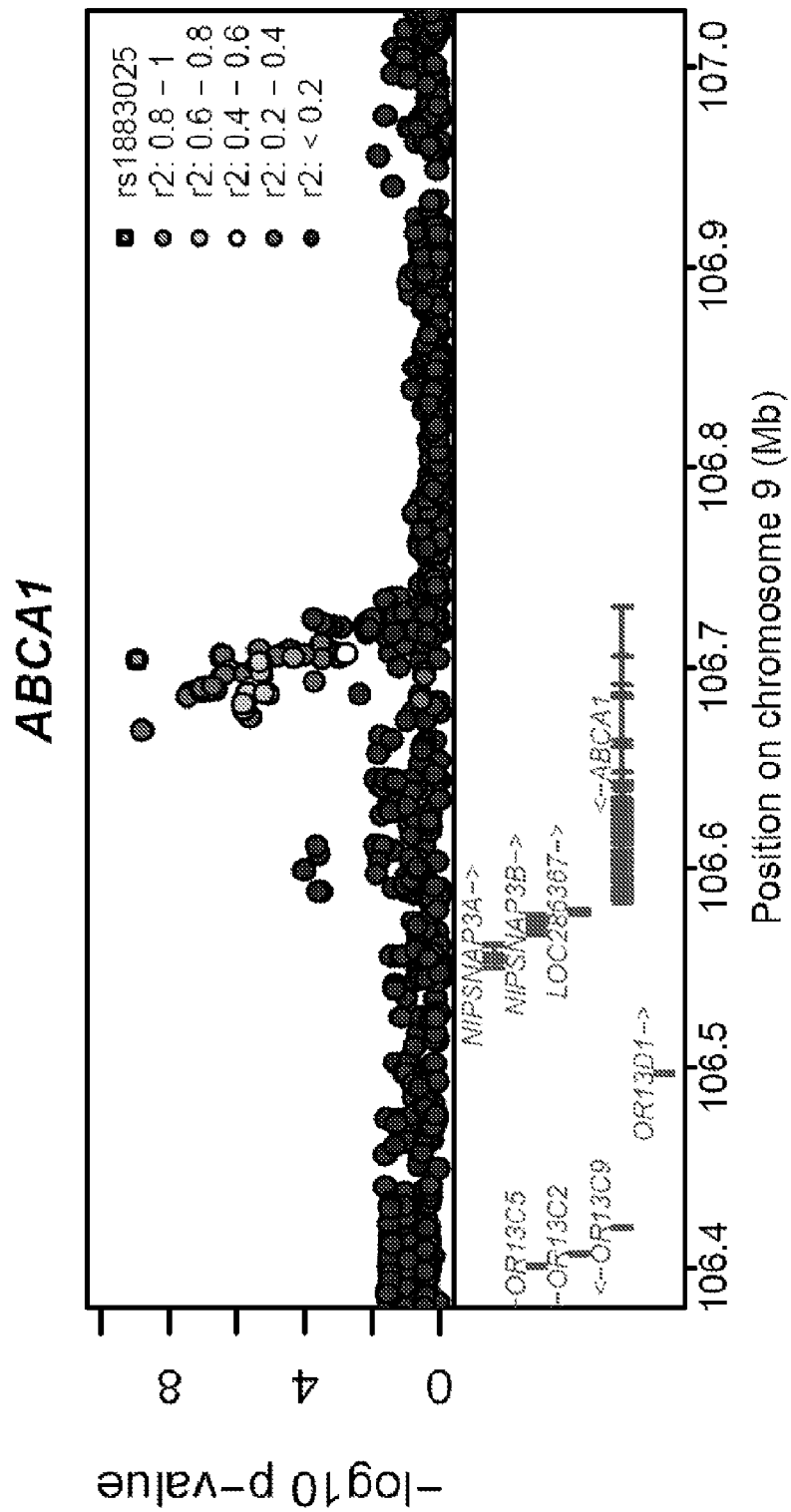
Figure 4:
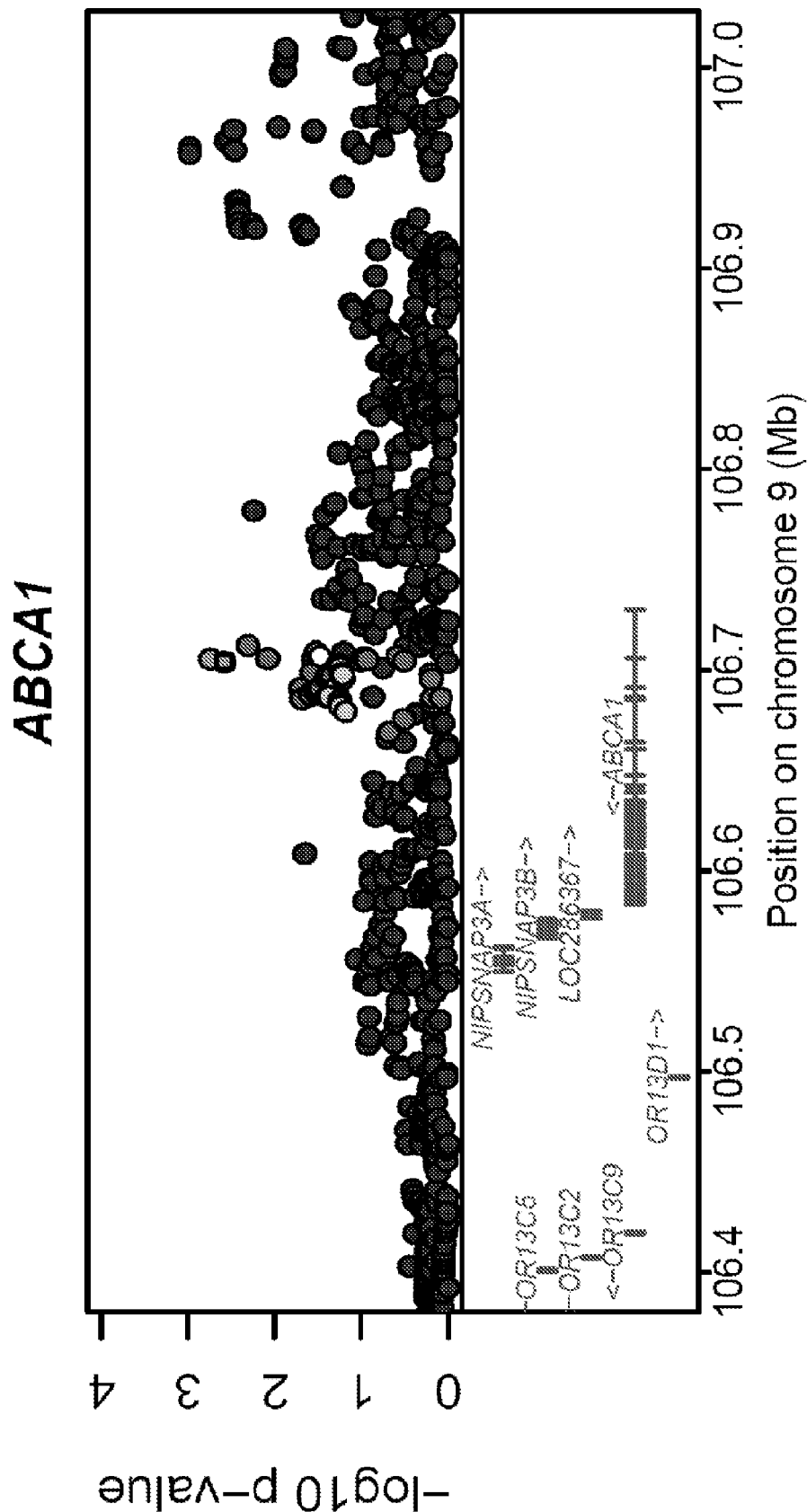

(2008), Kathiresan et al. Nature Genetics 41, 56-65 (2009), herein incorporated by reference in their entireties). A search was performed to examine whether other common HDL-cholesterol associated polymorphisms might contribute to AMD risk. The three common alleles showing strongest association to blood HDL-cholesterol levels (Kathiresan et al. Nature Genetics 41, 56-65 (2009), herein incorporated by reference in its entirety) show evidence of association with AMD (rs173539 near CETP with $p=2.4\times10^{-6}$ in the discovery sample; rs12678919 near LPL with $p=0.0016$; rs10468017 near LIPC with $p=0.0018$) (SEE FIG. 4, Table 5). Near CETP and LIPC, evidence of two common alleles, that are associated independently with HDL-cholesterol levels has been reported (Kathiresan et al. Nature Genetics 41, 56-65 (2009), herein incorporated by reference in its entirety). Modest association was identified between the secondary HDL-associated alleles in each of these loci with AMD (rs289714 near CETP with $p=0.062$; rs2070895 near LIPC with $p=0.051$). Finally, HDL-associated alleles near ABCA1 also show evidence of association with AMD (rs1883025, $p=0.0026$). The probability that four or more of the 14 reported HDL-associated alleles would show association with AMD with $p=0.0026$ or better by chance is extremely low ($4\times10^{-8}$), and the probability that the top three HDL-associated alleles would reveal association with $p=0.0018$ or better is $6\times10^{-9}$. Association was identified specifically for alleles with the largest impact on HDL levels, indicating that additional signals may exist. Evidence for association at CETP, LPL, and ABCA1 was consistent in follow-up samples and the discovery cohort; combining all available data observed association with $p=1.6\times10^{-6}$ near CETP, $p=8.9\times10^{-4}$ near LPL, and $4.4\times10^{-4}$ near ABCA1; SEE Table 5).

incidence of AMD (Klein et al. Ophthalmology 100, 406-14 (1993), Tomany et al. Ophthalmology 111, 1280-7 (2004), herein incorporated by reference in their entireties). Cholesterol and lipids accumulate underneath the RPE with age and are present in drusen (Malek et al. Am J Pathol 162, 413-25 (2003), Mullins et al. FASEB J 14, 835-46 (2000), herein incorporated by reference in their entireties). It has been shown that 7-ketocholesterol, an oxidized cholesterol derivative, induces vascular endothelial growth factor (VEGF) expression in the retina (Moreira et al. Invest Opthalmol V is Sci 50, 523-32 (2009), herein incorporated by reference ion its entirety), a potentially key step in the development of neovascular disease. Experiments perform during development of embodiments of the present invention indicate an important role for HDL-cholesterol metabolism in the pathogenesis of AMD but that, perhaps, HDL-cholesterol levels in blood are not the best proxy for the impact of this risk factor on disease susceptibility.

In the discovery sample, evidence of interactions between associated alleles at the seven loci listed in Tables 2 and 3 was not found. Interactions between risk alleles and age, sex and smoking were also not identified. Although all confirmed risk alleles were associated with all disease subtypes, strong evidence indicates that the ARMS2 locus preferentially increases risk of neovascular disease (OR=1.8, $p=1.8\times10^{-11}$ when compared to cases with large drusen; OR=1.4, $p=0.0009$ when compared to cases with geographic atrophy) and that the CFH locus preferentially increases the risk of geographic atrophy (OR=1.4, $p=0.0012$ when compared to cases with large drusen; OR=1.3, $p=0.009$ when compared to cases with neovascular disease) (Dewan et al. Science 314, 989-92 (2006). herein incorporated by reference in its

TABLE 5

Association results of loci associated with HDL-c

| SNP | Chrom. | Position (basepair) | Notable Nearby Genes | Alleles (risk/non-risk) | Frequency (risk allele) Cases | Frequency (risk allele) Controls | OR | p-value |
|---|---|---|---|---|---|---|---|---|
| rs3764261 | 16 | 55550825 | CETP | A/C | | | | |
| | Discovery sample (2,157 cases, 1,150 controls)... | | | | 0.364 | 0.314 | 1.36 | $1.4\times10^{-6}$ |
| | De novo replication sample (4,201 cases, 1484 controls)... | | | | 0.361 | 0.335 | 1.12 | 0.032 |
| | Combined sample (6,358 cases, 2,634 controls)... | | | | 0.362 | 0.326 | 1.17 | $1.6\times10^{-6}$ |
| rs12678919 | 8 | 19888502 | LPL | G/A | | | | |
| | Discovery sample (2,157 cases, 1,150 controls)... | | | | 0.115 | 0.096 | 1.38 | 0.0016 |
| | De novo replication sample (2,980 cases, 1,006, controls)... | | | | 0.104 | 0.089 | 1.19 | 0.13 |
| | Combined sample (5,137 cases, 2,156 controls)... | | | | 0.109 | 0.093 | 1.20 | $8.9\times10^{-4}$ |
| rs1883025 | 9 | 106704122 | ABCA1 | C/T | | | | |
| | Discovery sample (2,157 cases, 1,150 controls)... | | | | 0.739 | 0.705 | 1.25 | 0.0026 |
| | De novo replication sample (2,980 cases, 1,006, controls)... | | | | 0.758 | 0.735 | 1.13 | 0.058 |
| | Combined sample (5,137 cases, 2,156 controls)... | | | | 0.750 | 0.719 | 1.17 | $4.4\times10^{-4}$ |

While the alleles near CETP and LPL associated with decreased HDL-cholesterol levels in blood appear to increase the risk of AMD, the alleles near LIPC and ABCA1 associated with decreased HDL-cholesterol levels in blood appear to decrease the risk of AMD. CETP and LPL play major roles in the synthesis and degradation of HDL-cholesterol, whereas LIPC and ABCA1 are involved in mediating the uptake of HDL-cholesterol at the cell surface. CETP and ABCA1 are known to be expressed in the retina (Tserentsoodol et al. Mol Vis 12, 1319-33 (2006), herein incorporated by reference in its entirety), where evidence suggests they play a role in lipoprotein transport and processing.

Epidemiological studies have indicated a link between cardiovascular risk factors (including HDL-cholesterol) and entirety). All other alleles within these two loci showed no preferential association with the disease subtypes ($p>0.10$).

Genetic susceptibility variants may be used to predict individual risk of AMD (Seddon et al. Investigative Ophthalmology and Visual Science 50, (in print) (2009), Jakobsdottir et al. PLoS Genet 5, e1000337 (2009), herein incorporated by reference in their entireties). Individuals with high-risk multi-locus genotypes are nearly always affected with AMD. If genotypes are ordered according to the risk of AMD predicted in a logistic regression model by markers listed in Tables 2 and 3, among the 331 individuals with the highest risk genotypes in the sample, only 2 are controls and 329 are cases (SEE FIG. 5, top panel, for information on other genotype risk bands). Assuming a disease prevalence of 20% at age ~75, it is predicted that at the population level, ~80% of the individuals with risk genotypes in the top decile will develop AMD, but <5% of individuals in the bottom 3 deciles will develop disease (SEE FIG. 5, bottom panel). Furthermore, individuals with high risk genotypes will present with severe disease more frequently (among those in the top risk decile, 15% of cases have large drusen, whereas 22% have geographic atrophy, 43% have neovascularization, and 20% have both) than individuals with lower risk genotypes (among those in the bottom risk decile, 51% of cases have large drusen, 19% have geographic atrophy, 24% have neovascularization, and only 6% have both). Searches for rare alleles that impact disease susceptibility could start with a detailed examination of DNA sequences in the known risk susceptibility loci (e.g. CFH, ARMS2, C3, C2/CFB, CFI, TIMP3/SYN3 and LIPC) for individuals with severe disease but common variant genotypes that appear to confer low risk.

All publications and patents mentioned in the present application and/or listed below are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for characterizing a human subject as having an increased risk for developing age-related macular degeneration (AMD), said method comprising: detecting in a sample obtained from said subject the presence of at least one A allele of the rs9621532 single nucleotide polymorphism; wherein the presence of at least one A allele of the rs9621532 single nucleotide polymorphism is indicative of an increased risk for developing AMD.

2. The method of claim 1, further comprising detecting in said sample obtained from said subject the presence of one or more of: at least one A allele of the rs10737680 single nucleotide polymorphism, at least one G allele of the rs3793917 single nucleotide polymorphism, at least one G allele of the rs429608 single nucleotide polymorphism, at least one C allele of the rs2230199 single nucleotide polymorphism, at least one T allele of the rs2285714 single nucleotide polymorphism, at least one T allele of the rs1329424 single nucleotide polymorphism, at least one A allele of the rs9380272 single nucleotide polymorphism, and at least one C allele of the rs493258 single nucleotide polymorphism.

3. The method of claim 2, wherein said method comprises detecting the presence of two or more of: at least one A allele of the rs10737680 single nucleotide polymorphism, at least one G allele of the rs3793917 single nucleotide polymorphism, at least one G allele of the rs429608 single nucleotide polymorphism, at least one C allele of the rs2230199 single nucleotide polymorphism, at least one T allele of the rs2285714 single nucleotide polymorphism, at least one T allele of the rs1329424 single nucleotide polymorphism, at least one A allele of the rs9380272 single nucleotide polymorphism, and at least one C allele of the rs493258 single nucleotide polymorphism.

4. The method of claim 2, wherein said method comprises detecting the presence of five or more of: at least one A allele of the rs10737680 single nucleotide polymorphism, at least one G allele of the rs3793917 single nucleotide polymorphism, at least one G allele of the rs429608 single nucleotide polymorphism, at least one C allele of the rs2230199 single nucleotide polymorphism, at least one T allele of the rs2285714 single nucleotide polymorphism, at least one T allele of the rs1329424 single nucleotide polymorphism, at least one A allele of the rs9380272 single nucleotide polymorphism, and at least one C allele of the rs493258 single nucleotide polymorphism.

5. The method of claim 2, wherein said method comprises detecting the presence of seven or more of: at least one A allele of the rs10737680 single nucleotide polymorphism, at least one G allele of the rs3793917 single nucleotide polymorphism, at least one G allele of the rs429608 single nucleotide polymorphism, at least one C allele of the rs2230199 single nucleotide polymorphism, at least one T allele of the rs2285714 single nucleotide polymorphism, at least one T allele of the rs1329424 single nucleotide polymorphism, at least one A allele of the rs9380272 single nucleotide polymorphism, and at least one C allele of the rs493258 single nucleotide polymorphism.

6. The method of claim 2, wherein said method comprises detecting the presence of each of: at least one A allele of the rs10737680 single nucleotide polymorphism, at least one G allele of the rs3793917 single nucleotide polymorphism, at least one G allele of the rs429608 single nucleotide polymorphism, at least one C allele of the rs2230199 single nucleotide polymorphism, at least one T allele of the rs2285714 single nucleotide polymorphism, at least one T allele of the rs1329424 single nucleotide polymorphism, at least one A allele of the rs9380272 single nucleotide polymorphism, and at least one C allele of the rs493258 single nucleotide polymorphism.

* * * * *